United States Patent
Arnaout

(10) Patent No.: US 12,118,033 B2
(45) Date of Patent: Oct. 15, 2024

(54) SYSTEMS AND METHODS FOR MEDICAL IMAGE DIAGNOSIS USING MACHINE LEARNING

(71) Applicant: The Regents of the University of California, Oakland, CA (US)

(72) Inventor: Rima Arnaout, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 632 days.

(21) Appl. No.: 17/281,883

(22) PCT Filed: Sep. 18, 2019

(86) PCT No.: PCT/US2019/051767
§ 371 (c)(1),
(2) Date: Mar. 31, 2021

(87) PCT Pub. No.: WO2020/061218
PCT Pub. Date: Mar. 26, 2020

(65) Prior Publication Data
US 2022/0012875 A1    Jan. 13, 2022

Related U.S. Application Data

(60) Provisional application No. 62/733,045, filed on Sep. 18, 2018.

(51) Int. Cl.
*G06F 18/21* (2023.01)
*A61B 8/08* (2006.01)
(Continued)

(52) U.S. Cl.
CPC .......... *G06F 16/583* (2019.01); *G06F 18/217* (2023.01); *G06F 18/2431* (2023.01);
(Continued)

(58) Field of Classification Search
None
See application file for complete search history.

(56) References Cited

U.S. PATENT DOCUMENTS

2009/0034808 A1  2/2009  Zhou et al.
2010/0172567 A1  7/2010  Prokoski
(Continued)

FOREIGN PATENT DOCUMENTS

CA   3021697 A1   10/2017
EP   3853770 A1    7/2021
(Continued)

OTHER PUBLICATIONS

Extended European Search Report for European Application No. 19863399.2, Search completed May 20, 2022, Mailed Jun. 1, 2022, 9 Pgs.

(Continued)

*Primary Examiner* — Mohammed Rachedine
(74) *Attorney, Agent, or Firm* — KPPB LLP

(57) ABSTRACT

Systems and methods for medical image diagnoses in accordance with embodiments of the invention are illustrated. One embodiment includes a method for evaluating multimedia content. The method includes steps for receiving multimedia content and identifying a set of one or more image frames for each of several target views from the received multimedia content. For each target view, the method includes steps for evaluating the corresponding set of image frames to generate an intermediate result. The method includes steps for determining a composite result based on the intermediate results for each of the several target views.

19 Claims, 17 Drawing Sheets

(51) Int. Cl.
    *G06F 16/583* (2019.01)
    *G06F 18/2431* (2023.01)
    *G06T 7/00* (2017.01)
    *G06T 7/13* (2017.01)
    *G06V 10/44* (2022.01)
    *G06V 10/764* (2022.01)

(52) U.S. Cl.
    CPC .............. *G06T 7/0012* (2013.01); *G06T 7/13* (2017.01); *G06V 10/449* (2022.01); *G06V 10/764* (2022.01); *G06T 2207/10016* (2013.01); *G06T 2207/20132* (2013.01)

(56) References Cited

U.S. PATENT DOCUMENTS

| | | | |
|---|---|---|---|
| 2012/0092334 A1 | 4/2012 | Yoo | |
| 2012/0178070 A1* | 7/2012 | Wiegand | G16H 20/70 434/262 |
| 2013/0121571 A1 | 5/2013 | Gokturk et al. | |
| 2014/0050384 A1* | 2/2014 | Schmidt | G06T 7/0014 382/128 |
| 2015/0086947 A1* | 3/2015 | Schweid | G09B 5/06 434/219 |
| 2018/0137622 A1* | 5/2018 | Hiltl | G06T 7/248 |

FOREIGN PATENT DOCUMENTS

| | | | |
|---|---|---|---|
| IN | 201406295-14 | * | 8/2016 |
| KR | 1287382 B1 | * | 7/2013 |
| WO | 2018084071 A1 | | 5/2018 |
| WO | WO-2018187622 A1 | * | 10/2018 |
| WO | 2020061218 A1 | | 3/2020 |

OTHER PUBLICATIONS

International Preliminary Report on Patentability for International Application PCT/US2019/051767, Report issued Mar. 23, 2021, Mailed Apr. 1, 2021, 6 Pgs.

International Search Report and Written Opinion for International Application No. PCT/US2019/051767, Search completed Nov. 18, 2019, Mailed Dec. 3, 2019, 14 Pgs.

"AIUM Practice Guideline for the Performance of Fetal Echocardiography", Journal of Ultrasound in Medicine, vol. 32, No. 6, Jun. 2013, pp. 1067-1082.

"Practice Bulletin No. 175: Ultrasound in Pregnancy", Committee on Practice Bulletins, Obstetrics & Gynecology, vol. 128, No. 6, Dec. 2016, pp. e241-e256.

"WHO Guideline: recommendations on digital interventions for health system strengthening", Geneva: World Health Organization, 2019, 150 pgs.

Bensemlali et al.., "Neonatal management and outcomes of prenatally diagnosed CHDs", Cardiology in the Young, 2017, vol. 27, No. 2, pp. 344-353, doi:10.1017/S1047951116000639.

Best et al., "Long-term survival of individuals born with congenital heart disease: a systematic review and meta-analysis", Journal of the American Heart Association, 2016, vol. 5, No. 6, e002846, 16 pgs., doi: 10.1161/JAHA.115.002846.

Buethe et al., "Eponymous cardiovascular surgeries for congenital heart diseases—imaging review and historical perspectives", Current Problems in Diagnostic Radiology, Jul.-Aug. 2015, vol. 44, Issue 4, pp. 303-320, doi:10.1067 /j.cpradiol.2015.02.003.

Carvalho et al., "ISUOG Practice Guidelines (updated): sonographic screening examination of the fetal heart", Ultrasound in Obstetrics & Gynecology, 2013, vol. 41, No. 3, pp. 348-359, DOI: 10.1002/uog.12403.

Chu et al.., "Prenatal diagnosis of congenital heart diseases by fetal echocardiography in second trimester: a Chinese multicenter study", Acta Obstetricia et Gynecologica Scandinavica, Apr. 2017, vol. 96, No. 4, pp. 454-463, DOI: 10.1111/aogs.13085.

Corcoran et al., "Prenatal detection of major congenital heart disease—optimising resources to improve outcomes", European Journal of Obstetrics & Gynecology and Reproductive Biology, Aug. 1, 2016, vol. 203, pp. 260-263, first published Jun. 18, 2016, DOI:https://doi.org/10.1016/j.ejogrb.2016.06.008.

Donofrio et al., "Diagnosis and Treatment of Fetal Cardiac Disease A Scientific Statement from the American Heart Association", Circulation, May 27, 2014, vol. 129, No. 21, pp. 2183-2242, DOI: 10.1161/01.cir.0000437597.44550.5d.

Esteva et al., "Dermatologist-level classification of skin cancer with deep neural networks", Nature, Feb. 2, 2017, vol. 542, No. 7639, pp. 115-118, published online Jan. 25, 2017, doi: 10.1038/nature21056.

Freud et al.., "Fetal Aortic Valvuloplasty for Evolving Hypoplastic Left Heart Syndrome: Postnatal Outcomes of the First 100 Patients", Circulation, Aug. 19, 2014, vol. 130, No. 8, pp. 638-645, Doi: 10.1161/CIRCULATIONAHA.114.009032.

Friedberg et al.., "Prenatal detection of congenital heart disease", The Journal of pediatrics, Jul. 2009, vol. 155, No. 1, pp. 26-31, published online Apr. 24, 2009, doi: 10.1016/j.jpeds.2009.01.050.

Goldinfeld et al., "Evaluation of fetal cardiac contractility by two-dimensional ultrasonography", Prenatal Diagnosis, Oct. 2004, vol. 24, No. 10, pp. 799-803, doi: 10.1002/pd.880.

Gulshan et al., "Development and validation of a deep learning algorithm for detection of diabetic retinopathy in retinal fundus photographs", Journal of the American Medical Association, Dec. 13, 2016, vol. 316, No. 22, pp. 2402-2410, DOI: 10.1038/s41591-019-0536-x.

Holland et al.., "Prenatal diagnosis of critical congenital heart disease reduces risk of death from cardiovascular compromise prior to planned neonatal cardiac surgery: a meta-analysis", Ultrasound in Obstetrics & Gynecology, 2015, vol. 45, No. 6, pp. 631-638, DOI: 10.1002/uog.14882.

Jiang et al.., "To Trust or Not To Trust A Classifier", Advances in Neural Information Processing Systems, 2018, pp. 5541-5552.

Karpathy et al.., "Large-scale Video Classification with Convolutional Neural Networks", In: Proc. CVPR, 2014, 8 pgs., Doi: 10.1109/CVPR.2014.223.

Kulhare et al.., "Key Frame Extraction for Salient Activity Recognition", IEEE, 23rd International Conference on Pattern Recognition (ICPR), 2016, pp. 835-840.

Lecun et al.., "Deep learning", Nature, May 27, 2015, vol. 521, No. 7553, pp. 436-444, doi: 10.1038/nature14539.

Letourneau et al., "Advancing Prenatal Detection of Congenital Heart Disease: A Novel Screening Protocol Improves Early Diagnosis of Complex Congenital Heart Disease", Journal of Ultrasound in Medicine, Oct. 13, 2017, vol. 37, No. 5, pp. 1073-1079, doi: 10.1002/jum.14453.

Li et al., "Efficacy of prenatal diagnosis of major congenital heart disease on perinatal management and perioperative mortality: a meta-analysis", World Journal of Pediatrics, Aug. 15, 2016, vol. 12, No. 3, pp. 298-307, first published Apr. 8, 2016, doi: 10.1007/s12519-016-0016-z.

Liu et al.., "Fetal echocardiography for congenital heart disease diagnosis: a meta-analysis, power analysis and missing data analysis", European Journal of Preventive Cardiology, Sep. 25, 2014, vol. 22, No. 12, pp. 1531-1547, DOI: 10.1177/2047487314551547.

Madani et al., "Fast and accurate classification of echocardiograms using deep learning", npj | Digital Medicine, Mar. 21, 2018, vol. 1, No. 6, 31, pgs., doi:10.1038/s41746-017-0013-1.

Miceli, "A review of the diagnostic accuracy of fetal cardiac anomalies", Australasian Journal of Ultrasound in Medicine, Feb. 2015, vol. 18, No. 1, pp. 3-9.

Oster, "A population-based study of the association of prenatal diagnosis with survival rate for infants with congenital heart defects", The American Journal of Cardiology, Mar. 15, 2014, vol. 113, No. 6, pp. 1036-1040, doi:10.1016/j.amjcard.2013.11.066.

Pinheiro et al.., "Accuracy of Prenatal Diagnosis of Congenital Cardiac Malformations: Acurácia do diagnóstico pré-natal de cardiopatias congênitas", Rev. Bras. Ginecol. Obstet., Jan. 2019, vol. 41, No. 1, published online: Dec. 14, 2018, pp. 11-16, https://doi.org10.1055/s-0038-1676058.

Ronneberger et al., "U-net: Convolutional networks for biomedical image segmentation", International Conference on Medical image

(56) References Cited

OTHER PUBLICATIONS computing and computer-assisted intervention, Springer, Cham, 2015, pp. 234-241, arXiv:1505.04597 [cs.CV], May 18, 2015.

Russakovsky et al.., "ImageNet Large Scale Visual Recognition Challenge", arXiv:1409.0575v3 [cs.CV], Jan. 30, 2015, 43 pgs.

Sekar et al.., "Diagnosis of congenital heart disease in an era of universal prenatal ultrasound screening in southwest Ohio", Cardiology in the Young, vol. 25, No. 1 (2015) pp. 35-41, doi:10.1017/S1047951113001467.

Sizarov et al., "Valve interventions in utero: understanding the timing, indications, and approaches", Canadian Journal of Cardiology, Sep. 1, 2017, vol. 33, pp. 1150-1158, published online Jun. 22, 2017, doi:10.1016/j.cjca.2017.06.009.

Sklansky et al.., "Fetal Cardiac Screening: What Are We (and Our Guidelines) Doing Wrong?", Journal of Ultrasound in Medicine, Apr. 2016, vol. 35, No. 4, pp. 679-681, doi:10.7863/ultra.15.07021.

Sun et al.., "Prenatal detection of critical cardiac outflow tract anomalies remains suboptimal despite revised obstetrical imaging guidelines", Congenital Heart Disease, Sep./Oct. 2018, vol. 13, No. 5, pp. 748-756, https://doi.org/10.1111/chd.12648.

Tunçalp et al., "WHO recommendations on antenatal care for a positive pregnancy experience-going beyond survival", BJOG: An International Journal of Obstetrics & Gynaecology, May 2017, vol. 124, No. 6, pp. 860-862, published online Mar. 9, 2017, DOI: 10.1111/1471-0528.14599.

Wright et al.., "Relation of prenatal diagnosis with one-year survival rate for infants with congenital heart disease", The American journal of cardiology, Mar. 15. 2014, vol. 113, No. 6, pp. 1041-1044, https://doi.org/10.1016/j.amjcard.2013.11.065.

Zech et al.., "Variable generalization performance of a deep learning model to detect pneumonia in chest radiographs: A cross-sectional study", PLOS Medicine, Nov. 6, 2018, vol. 15, No. 11, e1002683, 17 pgs., https://doi.org/10.1371/journal.pmed.1002683.

Zhao et al., "Cardiac axis shift within the cardiac cycle of normal fetuses and fetuses with congenital heart defect", Ultrasound in Obstetrics & Gynecology, 2015, vol. 46, No. 5, pp. 558-563, DOI: 10.1002/uog.14768.

Zhao et al., "Fetal cardiac axis in tetralogy of Fallot: associations with prenatal findings, genetic anomalies and postnatal outcome", Ultrasound in Obstetrics & Gynecology, 2017, vol. 50, No. 1, pp. 58-62, published online Jun. 6, 2017, DOI: 10.1002/uog.15998.

\* cited by examiner

SYSTEMS AND METHODS FOR MEDICAL IMAGE DIAGNOSIS USING MACHINE LEARNING

CROSS-REFERENCE TO RELATED APPLICATIONS

The current application is a U.S. national phase of PCT Application No. PCT/US2019/051767 entitled, "Systems and Methods for Medical Image Diagnosis Using Machine Learning", filed Sep. 18, 2019, which claims the benefit of and priority under 35 U.S.C. § 119(e) to U.S. Provisional Patent Application No. 62/733,045 entitled "Echocardiogram Diagnosis Using Machine Learning" filed Sep. 18, 2018. The disclosures of PCT Application No. PCT/US2019/051767 and U.S. Provisional Patent Application No. 62/733,045 are hereby incorporated by reference in their entirety for all purposes.

This invention was made with government support under grant no. K08 HL125945 awarded by The National Institutes of Health. The government has certain rights in the invention.

FIELD OF THE INVENTION

The present invention generally relates to evaluating medical images and, more specifically, to the capture and analysis of ultrasound images for diagnosis and treatment of health conditions.

BACKGROUND

Medical imaging is key to diagnosis and management in medicine. Common medical imaging modalities include (but are not limited to) photography, X-ray, computed tomography, magnetic resonance imaging, nuclear imaging, and ultrasound. Ultrasound uses high-frequency sound waves to produce images of structures inside a body, such as (but not limited to) a heart, blood vessels, kidneys, and many other organs. Among medical imaging modalities, ultrasound is ubiquitous due to its non-invasive nature, low cost, and absence of radiation. Ultrasound is an information-rich phenotyping modality that provides both structural and functional information in real time. Like other medical imaging modalities, ultrasound images can be used to diagnose and manage various conditions.

For example, ultrasounds of the heart (echocardiograms) are necessary in diagnosis and management of virtually every cardiac disease. It is often the entry test for cardiac disease suspected by clinical story, examination, and electrocardiogram, and a normal echocardiogram alone can definitively rule out many cardiac conditions. As another example, fetal screening ultrasounds can be used to diagnose congenital heart disease (CHD). One percent of babies are born with congenital heart malformations, making congenital heart disease the most common type of birth defect. CHD can be asymptomatic in fetal life but cause significant morbidity and mortality after birth. Early diagnosis of CHD can give better results for a patient (specifically, can decrease neonatal shock and neurologic morbidity); doctors are finding that fixing serious heart defects before a fetus is even born may potentially give them an even better quality of life, with the world's first fetal heart intervention performed in 1989. Today, surgery and other medical therapies can give babies with complex congenital heart disease a chance to live that is unprecedented in history. However, as with adult echocardiography and many other medical conditions, reaching this potential requires proper ultrasound diagnosis—and that process is still of variable, and sometimes poor, quality.

Despite its wide utility, ultrasound suffers from a lack of diagnostic accuracy and precision, especially when practitioners are undertrained. In echocardiography, for example, diagnostic error from under- or over-estimation of valve disease severity, pulmonary pressures, or chamber size and function have been well documented, can cause serious harm, and persist despite the existence of guidelines meant to avoid them. Additionally, sensitivity and specificity of fetal screening ultrasound for detection of major congenital heart defects varies widely, with the sensitivity of prenatal diagnosis ranging from 0% to 82% depending on the type of heart condition. Specificity of fetal ultrasound screening for heart defects is also low, about 40-50%.

While some errors are undoubtedly due to poor image acquisition, evidence shows that poor image interpretation by undertrained physicians also hampers accurate and precise diagnosis. Human interpretation also limits the speed and scale of image analysis, which is a glaring bottleneck at a time when the volume of medical imaging tests ordered is increasing steadily and outstripping the number of trained readers, especially in underdeveloped or rural areas. There is therefore a critical need to provide improved medical image interpretation at a scale and speed that humans cannot meet. One need critical to unburdening trained readers and providing essential medical information to providers on the front lines of healthcare, is to provide a scalable means to accurately interpret ultrasounds.

SUMMARY OF THE INVENTION

Systems and methods for medical image diagnoses in accordance with embodiments of the invention are illustrated. One embodiment includes a method for evaluating multimedia content. The method includes steps for receiving multimedia content and identifying a set of one or more image frames for each of several target views from the received multimedia content. For each target view, the method includes steps for evaluating the corresponding set of image frames to generate an intermediate result. The method includes steps for determining a composite result based on the intermediate results for each of the several target views.

In a further embodiment, the multimedia content includes video from a medical imaging test.

In still another embodiment, identifying the set of image frames includes deconstructing video from the multimedia content into individual image frames and processing each of the individual image frames.

In a still further embodiment, processing an image frame includes performing at least one of edge detection, cropping, and downsampling.

In yet another embodiment, identifying the set of one or more image frames for each target view includes classifying image frames from the multimedia content according to one of the several target views.

In a yet further embodiment, classifying the image frames includes classifying image frames as non-target views.

In another additional embodiment, evaluating the corresponding set of image frames includes using a separate evaluation model for each target view of the several target views.

In a further additional embodiment, each separate evaluation model for each target view includes a classification model trained to reach a same result as the composite result.

In another embodiment again, evaluating the corresponding set of image frames includes using several evaluation models for at least one target view of the several target views, where the several evaluation models include a segmentation model for segmenting image frames of the corresponding set of image frames.

In a further embodiment again, evaluating the corresponding set of image frames includes measuring a size of at least one segment in at least two different frames to compute a change in the segment.

In still yet another embodiment, the segmenting image frames includes segments of empty space within an image frame.

In a still yet further embodiment, determining the composite result includes using a composite model, wherein the composite model takes as input an output of the separate evaluation model for at least one target view of the several target views.

In still another additional embodiment, determining the composite result includes using a composite model, wherein the composite model takes as input at least one of a segmentation map, a measurement of a region of interest from at least one image, and a classification from the separate evaluation model for at least one target view of the several target views.

In a still further additional embodiment, identifying a set of one or more image frames for each of several target views from the received multimedia content comprises evaluating image frames based on the several target views, determining whether the image frames for each target view are sufficient for diagnosis, and when the images for a particular target view are not sufficient, providing feedback to a user to capture additional video.

In still another embodiment again, evaluating image frames includes determining whether image frames of a quality level greater than a threshold value have been captured for each of the several target views, wherein the quality level is based on a confidence level for a classification.

One embodiment includes a non-transitory machine readable medium containing processor instructions for evaluating multimedia content, where execution of the instructions by a processor causes the processor to perform a process that comprises receiving multimedia content, identifying a set of one or more image frames for each of several target views from the received multimedia content, for each target view, evaluating the corresponding set of image frames to generate an intermediate result, and determining a composite result based on the intermediate results for each of the several target views.

Additional embodiments and features are set forth in part in the description that follows, and in part will become apparent to those skilled in the art upon examination of the specification or may be learned by the practice of the invention. A further understanding of the nature and advantages of the present invention may be realized by reference to the remaining portions of the specification and the drawings, which forms a part of this disclosure.

DETAILED DESCRIPTION

Figure 1:
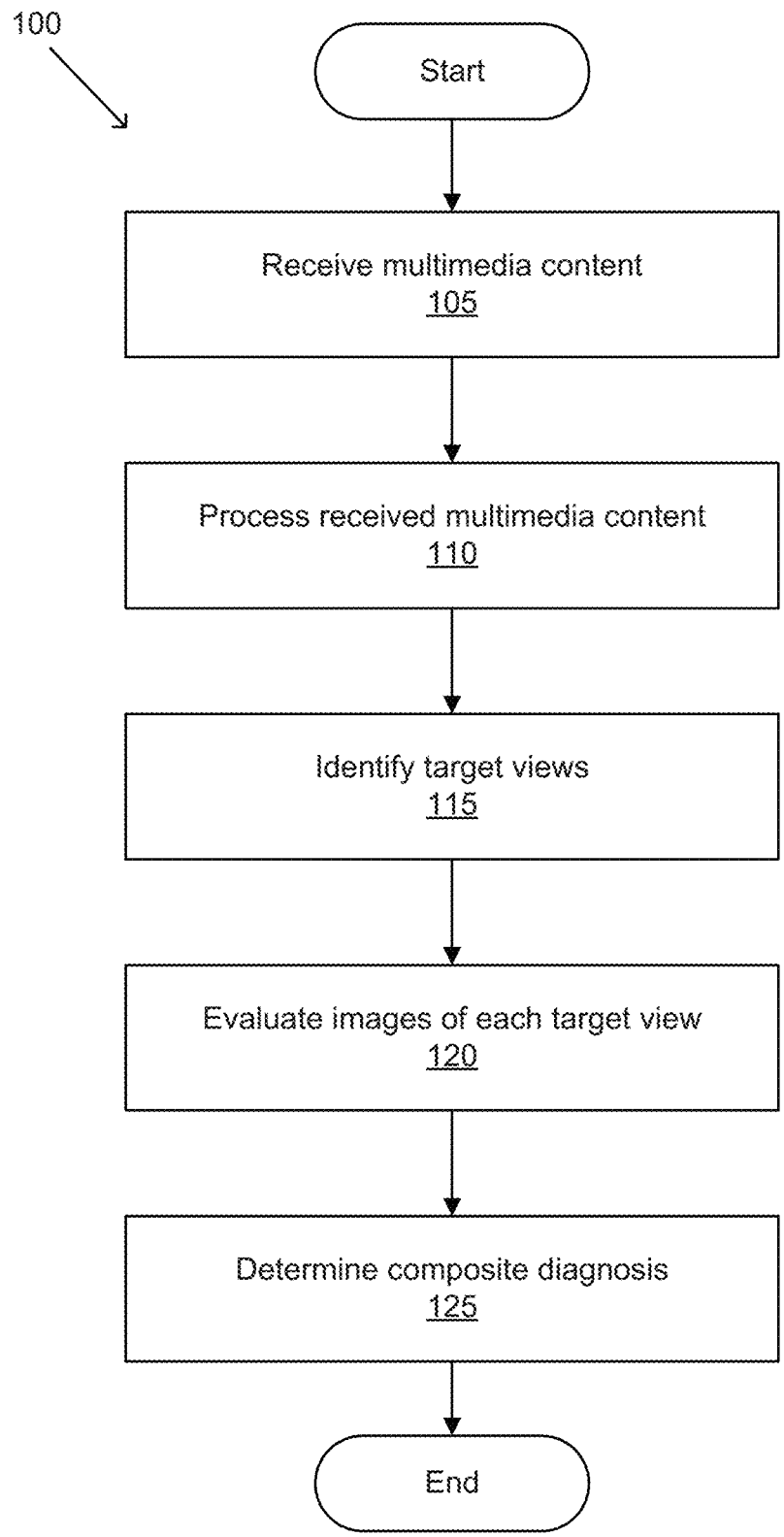
FIG. 1 conceptually illustrates a process for analyzing multimedia content in accordance with an embodiment of the invention.

Systems and methods for capturing multimedia content (e.g., video, images, etc.) for various medical imaging modalities in accordance with embodiments of the invention are disclosed. In various embodiments, a system for medical image capture can be used to capture and evaluate ultrasound images, such as echocardiograms and fetal screening ultrasounds. Systems in accordance with several embodiments of the invention can include a medical image capture element, an image analysis engine, and a feedback engine. Medical image capture elements in accordance with a number of embodiments of the invention can capture ultrasound images of a patient. In certain embodiments, image analysis engines employ a variety of machine learning techniques to determine a quality level of images captured by a capture element for use in diagnosis. Feedback engines in accordance with certain embodiments of the invention provide feedback and/or instructions to an operator of an ultrasound capture element to allow an operator to know when images sufficient for diagnosis have been captured.

Systems in accordance with several embodiments of the invention also include a diagnosis engine for diagnosing the captured images. In several embodiments, diagnosis engines include a number of machine learning models for evaluating the captured images to reach a diagnosis. Diagnosis engines in accordance with many embodiments of the invention can train separate models for each of a number of different views of a patient, in order to capture details from the different views of the patient. In numerous embodiments, a single machine learning model is trained on a compilation of the different views. Diagnosis engines in accordance with several embodiments of the invention include a composite model that receives the outputs of several machine learning models. Machine learning models can include (but are not limited to) machine learning models trained on each different view of a patient, and a structural model trained to analyze images for clinically relevant features (such as, but not limited to, valves, heart chambers, etc.), which can be fed into a composite model for generating a diagnosis.

Systems and methods in accordance with many embodiments of the invention can train an ensemble of machine learning models to identify target views, evaluate images to diagnose conditions (e.g., complex CHD lesions), and/or to identify regions of the images. In numerous embodiments, various measurements (e.g., cardiothoracic ratio (CTR), cardiac axis (CA), and/or fractional area change (FAC)) can be measured based on the identified regions. In testing, diagnostic models in accordance with certain embodiments of the invention achieved 89% sensitivity and 86% specificity in distinguishing normal hearts from abnormal hearts. Performance was shown to be comparable to expert clinicians and was similar on lower-quality images. Processes in accordance with a number of embodiments of the invention can significantly improve upon commonly reported sensitivity and specificity for disease detection using relatively few studies by (i) leveraging imaging from multiple different modalities for training, (ii) reducing the size of the input to only certain views from multimedia content for each imaging test, and (iii) breaking down the overall task into an ensemble of simpler steps. Such an approach can allow for computational efficiency both in training and in subsequent predictions on new data.

Evaluation

In numerous embodiments, medical imaging can be evaluated and analyzed to identify a number of target views of an area of interest (e.g., the heart). Where the multimedia content for an imaging test includes video clips, video in accordance with certain embodiments of the invention can be deconstructed to identify images (or frames) for each of the target views from the video. In a number of embodiments, target view identification can be performed in real-time, allowing the system to alert a practitioner when images for a particular target view have or have not yet been captured.

An example of a process for analyzing medical imaging in accordance with an embodiment of the invention is conceptually illustrated in FIG. 1. Process 100 receives (105) multimedia content. In certain embodiments, multimedia content is captured as a result of a set of one or more medical tests. Multimedia content in accordance with several embodiments of the invention, can include (but are not limited to) audio, video, as well as two-dimensional (2D) and/or three-dimensional (3D) images. In several embodiments, processes can be performed in real-time as a particular image or video is captured.

Process 100 processes (110) the multimedia content to identify input images. In various embodiments, after acquisition and upload, digital image and video data can go through a variety of processes, such as (but not limited to) extraction of digital image metadata (including clinical metadata), de-identification of images, conversion of multimedia content from compressed format to an uncompressed format, and/or normalization of greyscale and color values. In some embodiments, spatial and color resolution may be modified (downsampled) as needed for diagnosis. Processes in accordance with numerous embodiments of the invention can split video clips into constituent related frames for analysis and/or for downsampling of temporal resolution as needed. In a variety of embodiments, an edge detection step can be used to improve boundary detection for critical cardiac structures either before or after view classification. Processes in accordance with various embodiments of the invention can crop images around detected structures of interest to reduce background and to further improve performance both for measurements and for view classification. In many embodiments, processing can include various processes for data augmentation such as (but not limited to) shear, zoom, rotation, rescaling pixel values, etc.

Process 100 identifies (115) target view images from the input images. In certain embodiments, processes can perform a classification operation on the target view images to calculate a probability of the image belonging to each of several possible classes. Processes in accordance with many embodiments of the invention can classify each image to the class with the highest probability. In a number of embodiments, processes can identify multiple frames of a video (e.g., video segments) for a target view. Target views in accordance with numerous embodiments of the invention can include guideline-recommended views for diagnoses. For example, in the case of congenital heart disease (CHD) diagnoses, five axial views (3-vessel trachea (3VT), 3-vessel view (3VV), apical 5-chamber (A5C), apical 4-chamber (A4C), and abdomen (ABDO)) are recommended for detection.

Processes in accordance with many embodiments of the invention can identify one or more high-confidence images for each view. In numerous embodiments, high-confidence images are images that exceed a threshold value for classification within a certain class. In various embodiments, initial thresholds can be empirically chosen based on results from training data, where confidence probabilities assigned to each test image can help distinguish between (i) correct and incorrect predictions and (ii) images that belong to none of the target classes. For example, in some cases it can be shown that correct predictions often have probabilities over 0.95 and that a model frequently gets confused between particular classes (e.g., 3VV/3VT or A4C/A5C), where probabilities around 0.5 could describe uncertainly between two choices. In some embodiments, images with high probabilities (e.g., ≥0.95) for one of the view classes can be sorted to that class, while images with low probabilities (e.g., <0.4) can be sorted to a 'none of the above' class. In various embodiments, images with middling probabilities (e.g., from 0.4-0.94) can be manually classified by an expert labeler. An expert labeler can also review model-classified images and correct any errors. In several embodiments, all human-reviewed and human-classified images from the batch can then be added to the model's training set and the model can be retrained.

Process 100 evaluates (120) the target view images. Evaluating target view images in accordance with a variety of embodiments of the invention can include (but is not limited to) identifying image features, image segmentation, and/or measurements. In certain embodiments, processes can identify image features for images of each target view using a separate model trained for the particular target view. Models for evaluating each target view in accordance with some embodiments of the invention can identify features from images of the target view. In a number of embodiments, models can include (but are not limited to) convolutional neural networks (CNNs), recurrent neural networks (RNNs), and other architectures.

Figure 2:
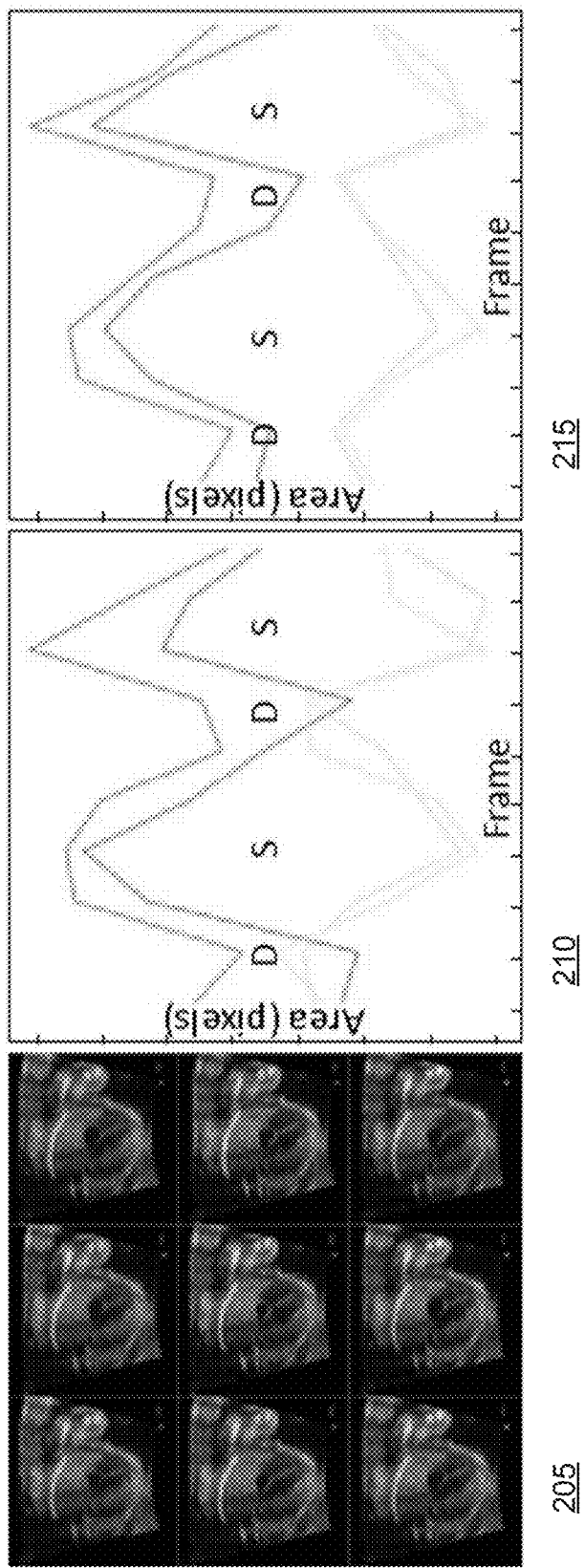
FIG. 2 illustrates examples of measurements from segmented portions in accordance with an embodiment of the invention.

In a number of embodiments, processes can segment images for evaluation and to find relevant structures in target view images. Segmented portions of an image can indicate various structures (or spaces), such as (but not limited to) thorax, heart, right atrium (RA), right ventricle (RV), left atrium (LA), left ventricle (LV), spine, and/or background pixels. Processes in accordance with several embodiments of the invention can evaluate the images and/or segmented portions of the images to determine various measurements. Segmented portions in accordance with several embodiments of the invention can be analyzed to determine various biometric measurements, such as (but not limited to) cardiothoracic ratio (CTR), cardiac axis (CA), and/or fractional area change (FAC) for each cardiac chamber. In numerous embodiments, target views can include multiple image frames (e.g., frames of the heart in ventricular systole and diastole), which can be used for measurements such as (but not limited to) a fractional area change calculation and/or plots of chamber area over time. Examples of measurements from segmented portions are illustrated in FIG. 2. Segmentation of image series 205 allows plots of chamber area over time (label, 210; prediction, 215) and identification of corresponding image frames in ventricular systole (S) and diastole (D) for fractional area change calculation.

In a number of embodiments, processes can aggregate (e.g., sum, average, median, etc.) evaluations (e.g., features, measurements, segments, etc.) for multiple images of a particular target view to determine an aggregate evaluation for the particular target view.

Process 100 determines (125) a composite diagnosis. In various embodiments, processes can take features from each of the target views, segmentation information, and/or measurements from one or more of the target views as input to a composite model. In various embodiments, composite models can take the fact that images from a target view were not captured (e.g., when no image frames exceed a threshold for a particular target view) as input to a composite model. Composite models in accordance with many embodiments of the invention can include one or more various models, such as (but not limited to) logistic regression, random forests, neural networks, etc.

Composite diagnoses (e.g., diagnosis of normal vs abnormal organ or anatomic structure) in accordance with some embodiments of the invention may take place first at the level of individual images or videos as sequential or related collections of still frames, and then an aggregation (e.g., sum, average, etc.) of these individual classifications from the different target views. This aggregation may be a simple summation, a weighted sum based on relative confidence probabilities assigned to each classification, or a majority rules or weighted majority rules approach. Alternatively, or conjunctively, several image and video views could be fed together to a single classification model. In various embodiments, multimedia content (e.g., an echocardiogram) from a medical imaging test could be represented as a single input to a deep learning model by concatenating several salient views as a single input.

Composite diagnostic models in accordance with a number of embodiments of the invention can output a diagnosis of normal vs abnormal for each medical imaging test and/or a confidence (probability estimation) that its classification was correct, to a healthcare provider. In a variety of embodiments, processes can further reassemble the images, generating new outputs, such as (but not limited to) video, 2D or 3D reconstructions, etc.

While specific processes for evaluating ultrasound images and/or video are described above, any of a variety of processes can be utilized to evaluate video as appropriate to the requirements of specific applications. In certain embodiments, steps may be executed or performed in any order or sequence not limited to the order and sequence shown and described. In a number of embodiments, some of the above steps may be executed or performed substantially simultaneously where appropriate or in parallel to reduce latency and processing times. In some embodiments, one or more of the above steps may be omitted. Although the above embodiments of the invention are described in reference to ultrasound images and video, the techniques disclosed herein may be used in any type of image/video evaluation, including medical photography, X-ray, computed tomography imaging, magnetic resonance imaging, and nuclear imaging.

Figure 3:
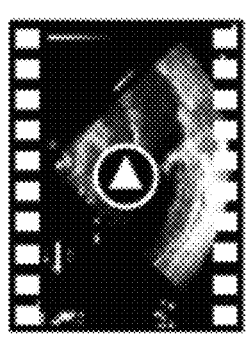
FIG. 3 illustrates examples of the multimodal nature of ultrasound imaging, which includes still images and videos from several different viewpoints, in accordance with an embodiment of the invention.
Figure 3:
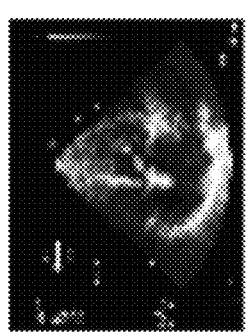
Figure 3:
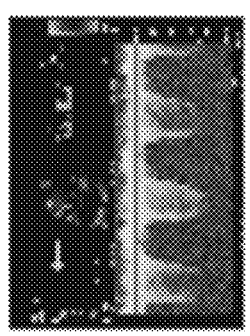
Figure 3:
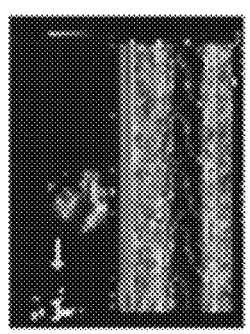
Figure 3:
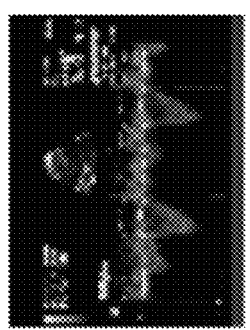
Figure 3:
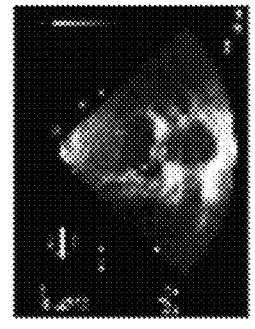
Figure 3:
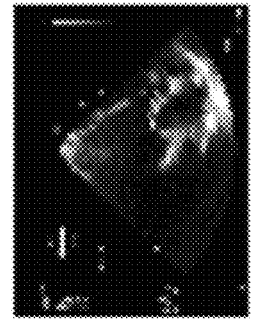
Figure 3:
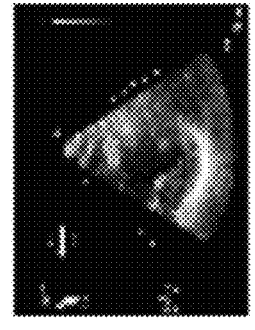
Figure 3:
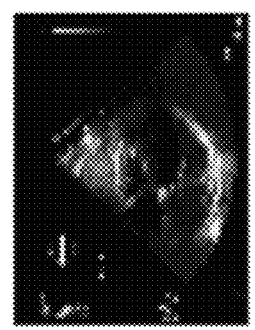
Figure 3:
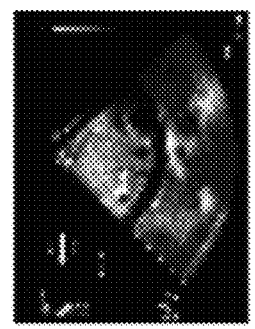

In a variety of embodiments, one or more different image modes can be used for diagnosing a condition. Examples of the multimodal nature of echocardiograms in accordance with an embodiment of the invention are illustrated in FIG. 3. In some embodiments, a combination of different acquisition methods can be used to obtain both morphologic and functional information on important structures for evaluation (e.g., chambers, vessels, and/or valves in a heart). These can include (but are not limited to) b-mode (2-dimensional) images and videos from different viewpoints, color Doppler and/or spectral Doppler to evaluate tissue and/or valve function, and/or m-mode to evaluate structures at high temporal resolution. This figure includes examples of a video clip 302, still images 304, m-mode 306, and pulsed-wave and continuous wave spectral Doppler recordings 308 and 310.

Within a single mode, multiple different views can be captured. This figure also illustrates several different acquisition views of the heart 312-320. Echocardiography presents limits on temporal, lateral, and axial resolution governed by the following relationships:

Temporal resolution $\alpha$ frame rate $\alpha$ 1/sector width a 1/depth

Lateral resolution=(radius of probe)$^2$/ultrasound wavelength

Axial resolution=spatial pulse length/2=0.77/ultrasound frequency

Figure 4:
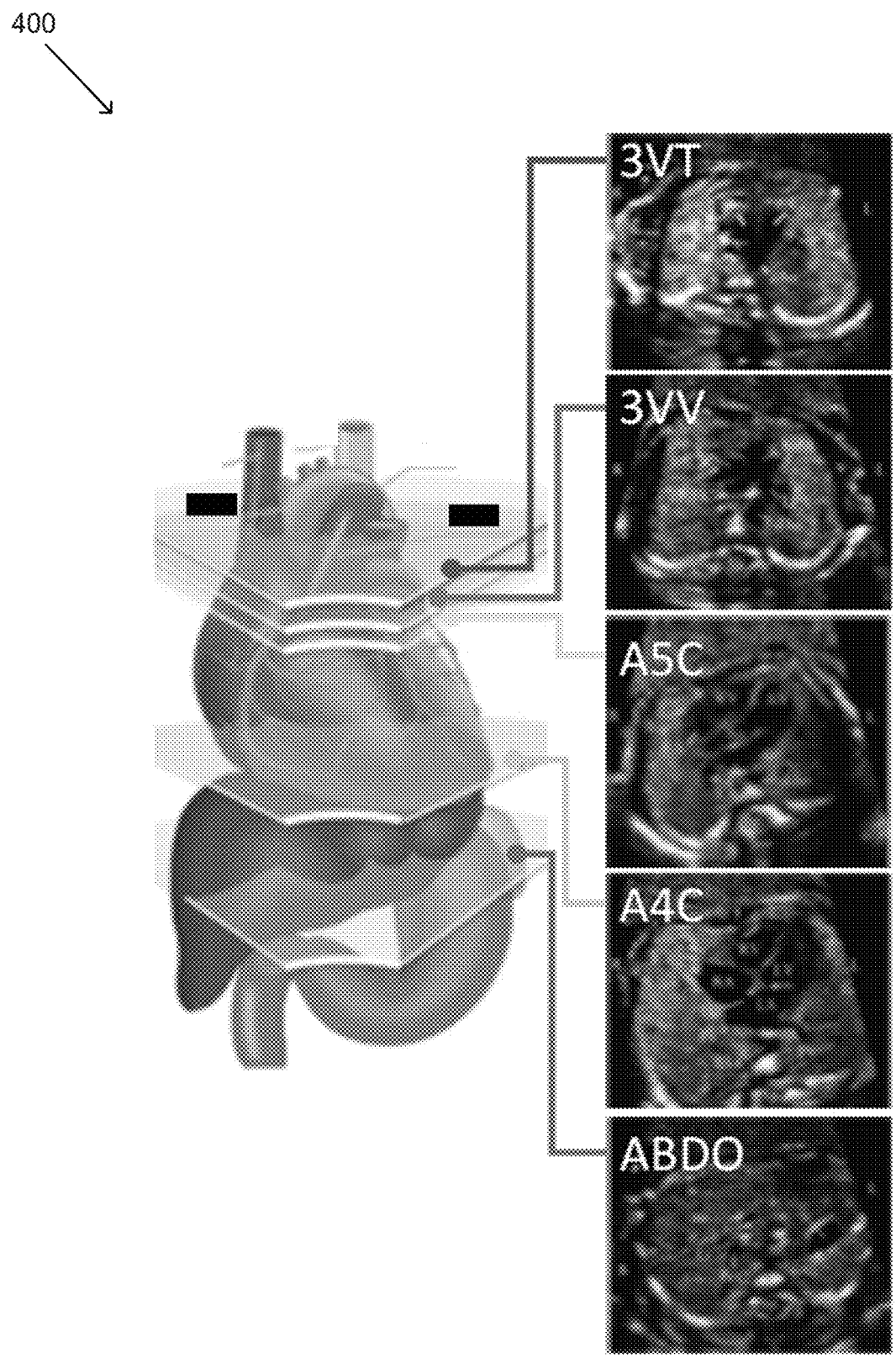
FIG. 4 illustrates examples of target view images in accordance with an embodiment of the invention.

Due to limitations on the movement of ultrasound waves through soft tissue, recordings of the three-dimensional heart can be acquired from different acquisition points, or views, in order to visualize all structures of the heart with the necessary temporal and spatial resolution for diagnosis. There are a number (e.g., at least 15 in adults) of different standard echocardiographic views. Examples of target view images in accordance with an embodiment of the invention are illustrated in FIG. 4. In this example, five different views (3-vessel trachea (3VT), 3-vessel view (3VV), apical 5-chamber (A5C), apical 4-chamber (A4C), and/or abdomen (ABDO)) and their positions within a heart are illustrated.

Figure 5:
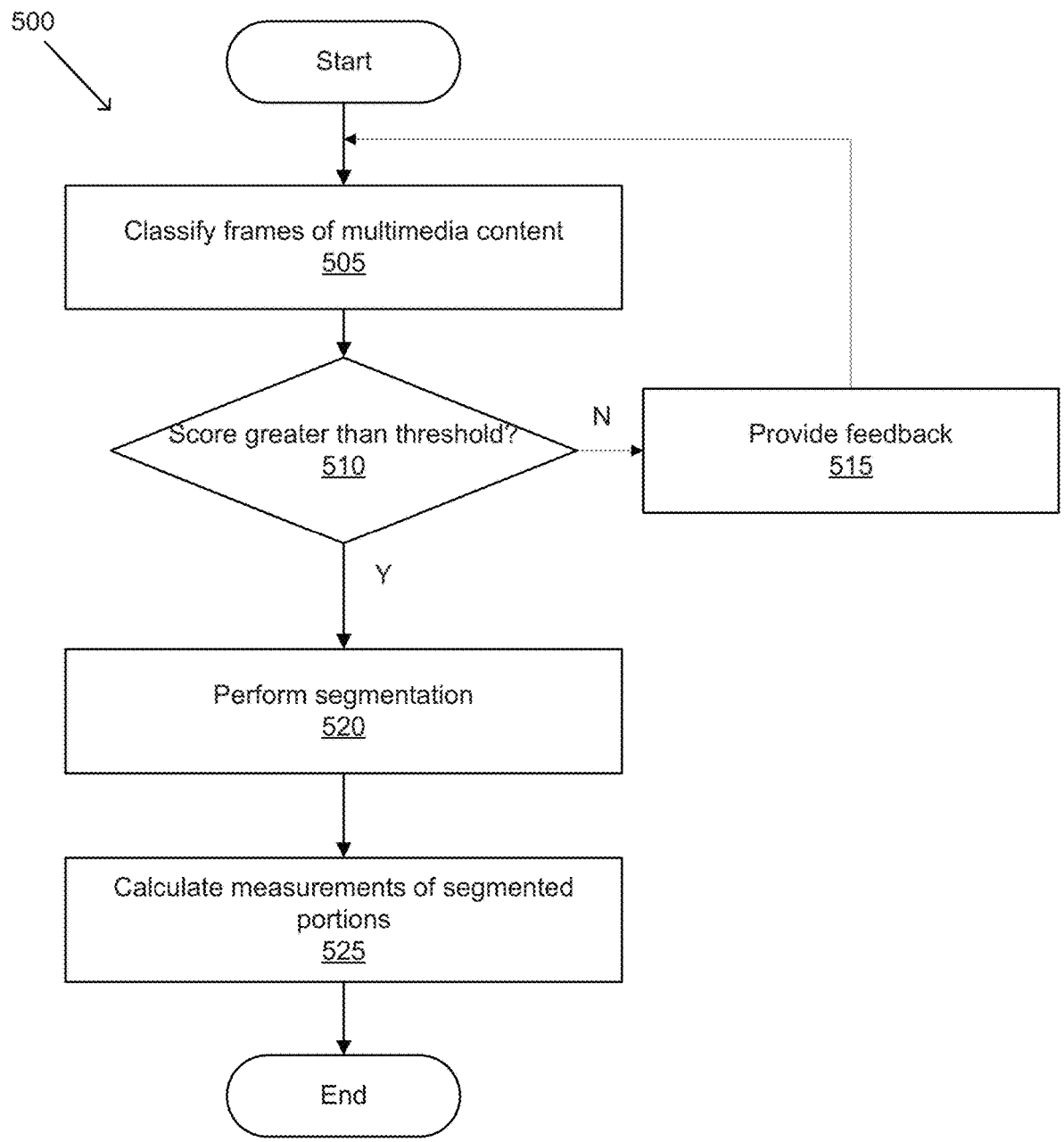
FIG. 5 conceptually illustrates a process for identifying and segmenting target view images in accordance with an embodiment of the invention.

A process for identifying and evaluating target view images in accordance with an embodiment of the invention is conceptually illustrated in FIG. 5. Process 500 classifies (505) frames of multimedia content. Classification of image frames in accordance with a variety of embodiments of the invention can be performed using a classifier model, such as (but not limited to) a neural network.

Process 500 determines (510) whether a score for each frame (or for a number of frames) is greater than a given threshold (e.g., 0.9). In several embodiments, processes can calculate a probability of an image belonging to each of multiple possible classes (e.g., target classes, non-target classes, etc.). Scores in accordance with numerous embodiments of the invention are determined with a classification model, where the scores can include a confidence score in a prediction.

When the process determines (510) that the score does not exceed the threshold, process 500 provides (515) feedback. In some embodiments, feedback can include a notification that a particular view has not yet been captured. Particularly in the case of abnormal hearts, it can often be difficult to ensure that an ultrasound contains quality images for each of the target views. Processes in accordance with various embodiments of the invention can provide instructions (e.g., visual guidance on a recommended angle and/or location for directing a user) to assist in the capture of a desired view. In many embodiments, processes can only provide feedback once a video capture has been completed, or periodically during an image capture. By selecting images with scores exceeding a threshold, the specificity for views of interest can be increased.

When the process determines (510) that the score does exceed the threshold, process 500 performs (520) a segmentation operation for identifying regions of an image. In a number of embodiments, processes can use a neural network to identify segmented portions or landmarks.

Process 500 calculates (525) measurements of the segmented portions. Segmented portions in accordance with several embodiments of the invention can be analyzed to determine various measurements of a heart. In numerous embodiments, target views can include multiple image frames (e.g., frames of the heart in ventricular systole and diastole), which can be used for measurements such as (but not limited to) a fractional area change calculation and/or plots of chamber area over time. Processes in accordance with many embodiments of the invention can perform segmentation and/or measurements (e.g., fetal cardiac biometrics) only on images from a subset (e.g., on the A4C) of the target views.

While specific processes for identifying and evaluating target view images are described above, any of a variety of processes can be utilized to evaluate target images as appropriate to the requirements of specific applications. In certain embodiments, steps may be executed or performed in any order or sequence not limited to the order and sequence shown and described. In a number of embodiments, some of the above steps may be executed or performed substantially simultaneously where appropriate or in parallel to reduce latency and processing times. In some embodiments, one or more of the above steps may be omitted.

Figure 6:
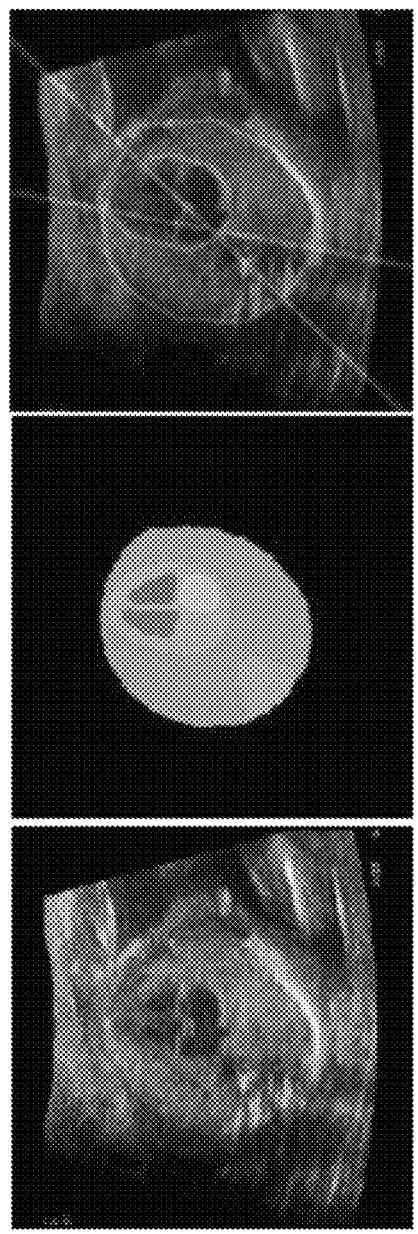
FIG. 6 illustrates examples of segmentation and measurements from ultrasound images in accordance with an embodiment of the invention.

Examples of segmentation and measurements from ultrasound images in accordance with an embodiment of the invention are illustrated in FIG. 6. In this example, the first image 605 illustrates an image from a ultrasound of a heart. The second image 610 illustrates a visualization of a segmentation of the heart image. The third image 615 illustrates measurements that can be computed from the heart image.

Figure 7:
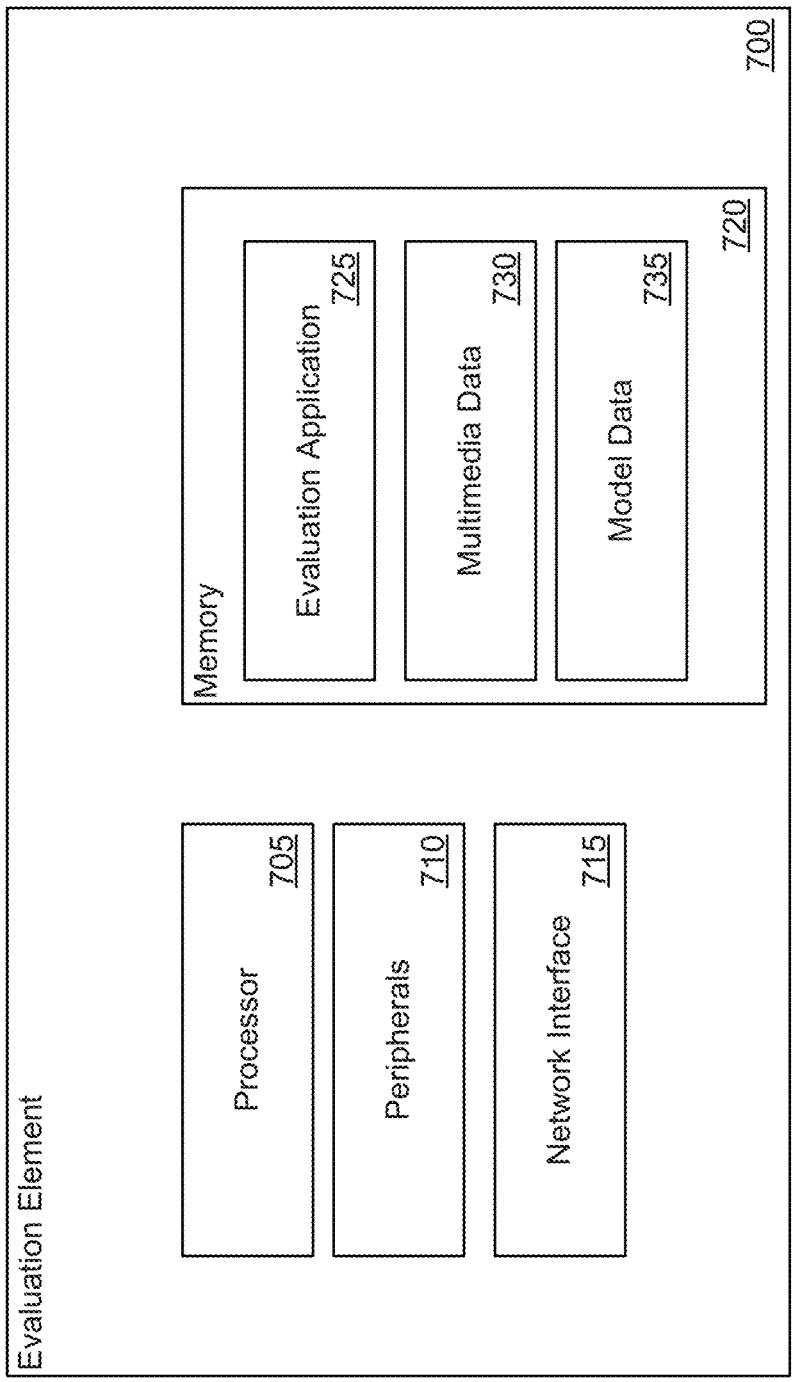
FIG. 7 illustrates an example of an evaluation element in accordance with an embodiment of the invention.

Processes for evaluating multimedia content in accordance with certain embodiments of the invention can be performed by evaluation elements in a system. An example of an evaluation element that executes instructions to perform processes that evaluate images or video in accordance with various embodiments of the invention is shown in FIG. 7. Evaluation elements in accordance with many embodiments of the invention can include (but are not limited to) one or more of mobile devices, cameras, and/or computers. evaluation element 700 includes processor 705, peripherals 710, network interface 715, and memory 720.

One skilled in the art will recognize that a particular evaluation element may include other components that are omitted for brevity without departing from this invention. The processor 705 can include (but is not limited to) a processor, microprocessor, controller, or a combination of processors, microprocessor, and/or controllers that performs instructions stored in the memory 720 to manipulate data stored in the memory. Processor instructions can configure the processor 705 to perform processes in accordance with certain embodiments of the invention.

Peripherals 710 can include any of a variety of components for capturing data, such as (but not limited to) cameras, displays, and/or sensors. In a variety of embodiments, peripherals can be used to gather inputs and/or provide outputs. For example, evaluation elements in accordance with several embodiments of the invention can be ultrasound capture devices or may be connected to such devices directly or over a network. Network interface 715 allows evaluation element 700 to transmit and receive data over a network based upon the instructions performed by processor 705. Peripherals and/or network interfaces in accordance with many embodiments of the invention can be used to gather inputs that can be used for evaluation and diagnosis.

Memory 720 includes an evaluation application 725, image data 730, and model data 735. Evaluation applications in accordance with several embodiments of the invention can be used to guide image captures, evaluate captured images, and/or generate diagnoses.

Multimedia data in accordance with a variety of embodiments of the invention can include various types of multimedia data that can be used in evaluation processes. In certain embodiments, multimedia data can include (but is not limited to) video, images, radio frequency data, spectral data, audio, etc.

In several embodiments, model data can store various parameters and/or weights for ensemble models. Model data in accordance with many embodiments of the invention can be updated through training on multimedia data captured on the evaluation element, or can be trained remotely and updated at the evaluation element.

Although a specific example of an evaluation element 700 is illustrated in FIG. 7, any of a variety of evaluation elements can be utilized to perform processes similar to those described herein as appropriate to the requirements of specific applications in accordance with embodiments of the invention.

Figure 8:
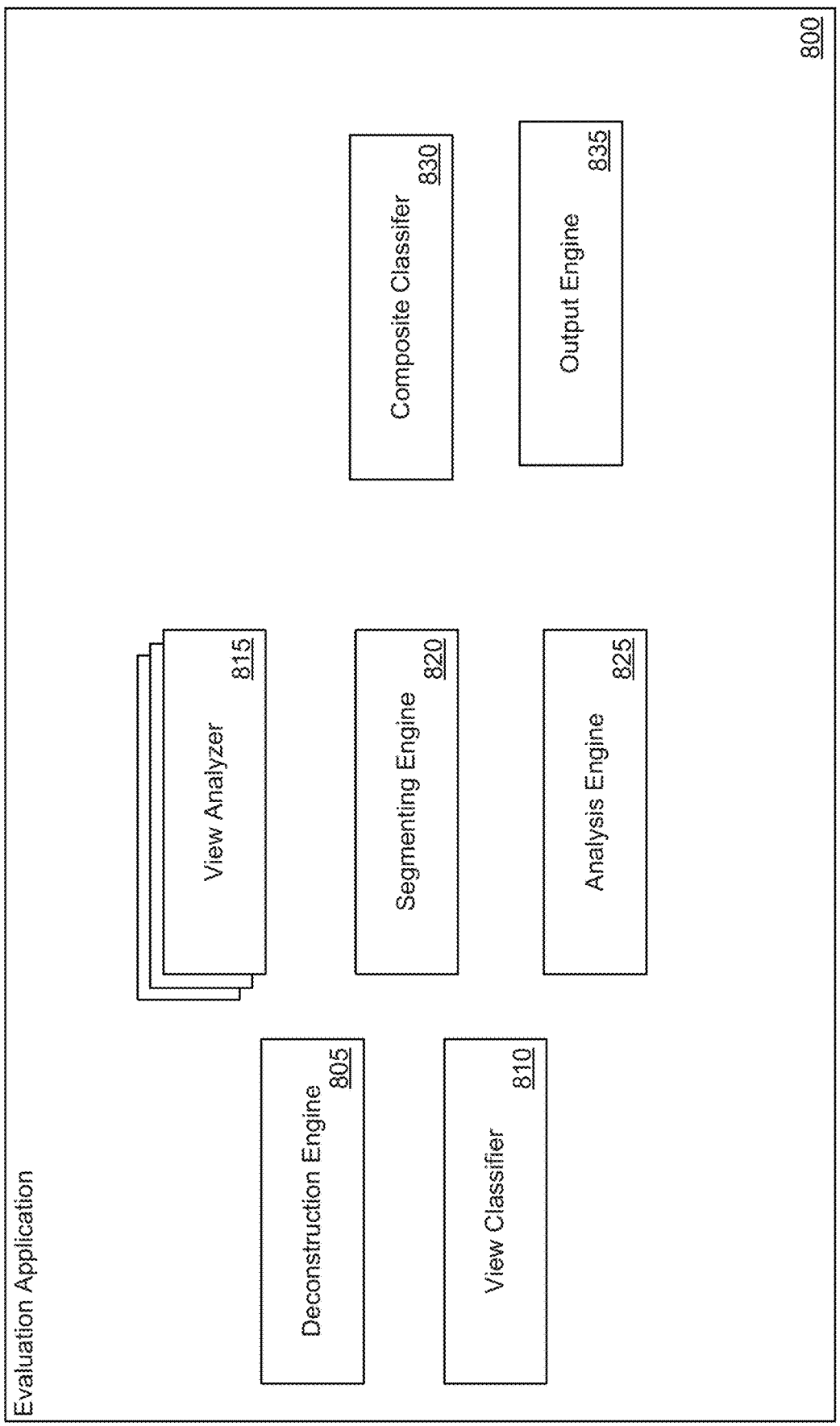
FIG. 8 illustrates an example of an evaluation application in accordance with an embodiment of the invention.

An example of an evaluation application for evaluating video in accordance with an embodiment of the invention is illustrated in FIG. 8. Evaluation application 800 includes deconstruction engine 805, view classifier 810, view analyzers 815, segmenting engine 820, analysis engine 825, composite classifier 830, and output engine 835.

Deconstruction engines in accordance with a variety of embodiments of the invention can deconstruct video into individual frames (or images). In certain embodiments, deconstruction engines can downsample the image resolution and/or temporal resolution prior to processing.

In many embodiments, view classifiers can classify individual deconstructed images (or frames) as being from one of a number of target views. View classifiers in accordance with a number of embodiments of the invention can determine whether an image is from a non-target view. In numerous embodiments, view classifiers can identify a best image for each of the target views. Alternatively, view classifiers in accordance with some embodiments of the invention can identify all images with a classification score greater than a threshold value for each target view.

View analyzers in accordance with several embodiments of the invention can include a separate view analyzer for each of a number of target views. In several embodiments, view analyzers can be used to evaluate one or more images from each view to produce a result, such as (but not limited to) a feature vector, diagnosis prediction, classification, etc. View analyzers in accordance with certain embodiments of the invention are trained to classify an image (e.g., normal vs. abnormal) so that the model learns important features. In some embodiments, classification layers (e.g., fully connected layers) can be removed from the trained view analyzers to produce feature vectors that encode important features of the images from each view.

In many embodiments, segmenting engines can segment images for evaluation, identifying important segments (or regions of interest) within each image. Segmented portions can be used as inputs to a composite classifier, or can be further processed by an analysis engine to compute measurements (e.g., CTR, CA, and/or FAC) that can be used by the composite classifier. In numerous embodiments, segmenting engines can be trained to identify empty space as a segment, where the empty space can be used in the evaluation process.

Analysis engines in accordance with many embodiments of the invention can analyze images (or segmented portions of images) to compute measurements for various elements within the images. For example, in the case of heart images, measurements can include (but are not limited to) cardiothoracic ratio (CTR), cardiac axis (CA), and/or fractional area change (FAC).

In certain embodiments, composite classifiers can take inputs from segmenting engines, analysis engines, and/or view analyzers to generate a composite analysis (e.g., a diagnosis). Composite classifiers in accordance with certain embodiments of the invention can include various methods such as (but not limited to) logistic regression, random forests, neural networks, etc. that is trained to classify images based on feature vectors, segments, and/or measurements from frames of a video from a number of different target views.

Output engines in accordance with several embodiments of the invention can provide a variety of outputs to a user, including (but not limited to) selected target views, diagnosis scores, confidence levels, notifications, and/or alerts. For example, output engines in accordance with various embodiments of the invention can provide a notification when no images from a particular target view have been captured (e.g., no image has been classified with a confidence level exceeding a threshold), alerting a user that they may want to recapture video for the particular target view.

Although a specific example of an evaluation application is illustrated in FIG. 8, any of a variety of evaluation applications (e.g., with more or fewer modules) can be utilized to perform processes similar to those described herein as appropriate to the requirements of specific applications in accordance with embodiments of the invention.

Deep learning models applied for view classification, segmentation, measurement, and/or diagnosis, of multimedia content, may vary and may include (but are not limited to) single convolutional neural networks, time information fusions neural networks, and/or multi-resolution neural networks. For each of these neural networks, the neural network may consist of different types and numbers of filters and layers. In some embodiments, models can include capsule networks and/or other machine learning architectures.

Figure 9:
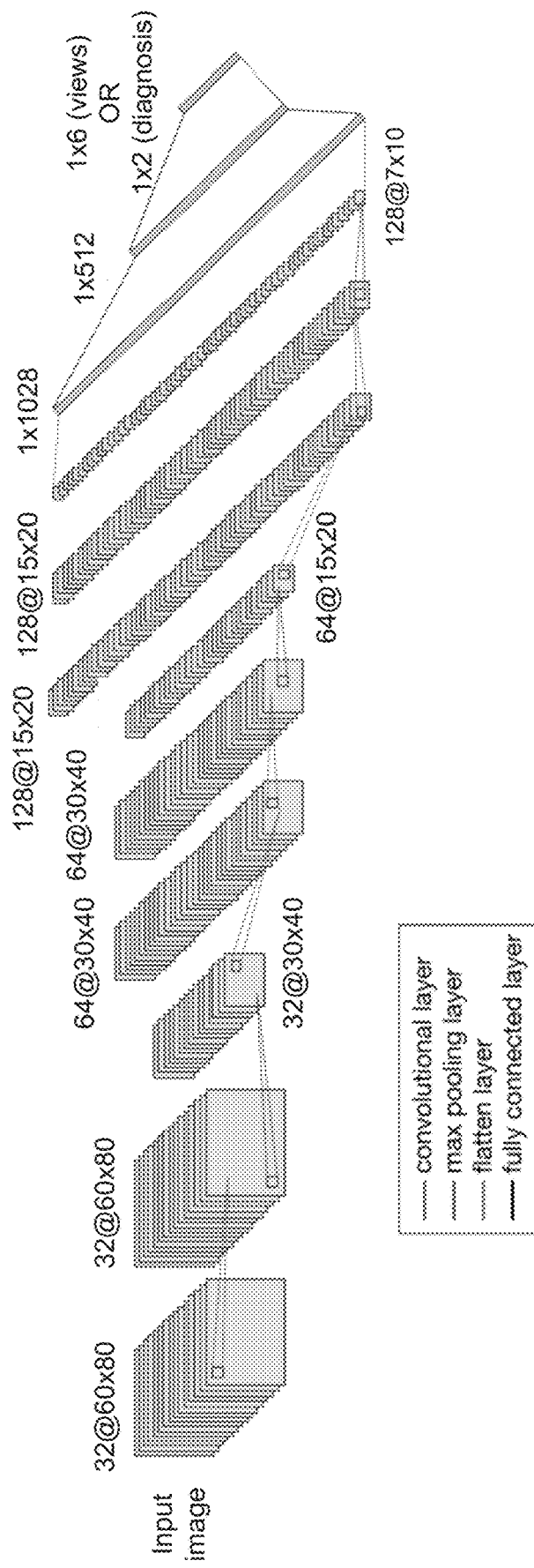
FIG. 9 illustrates an example architecture for classification models in accordance with an embodiment of the invention.

An example architecture for classification models in accordance with an embodiment of the invention is illustrated in FIG. 9. In this example, the model is composed of a number of alternating convolutional layers and max pooling layers, followed by a flattening layer and fully connected layers. In many embodiments, a flattening layer, max pooling layer, and/or convolutional layer can be used as a feature vector for a given image, and can be fed into a composite model for diagnosis.

Figure 10:
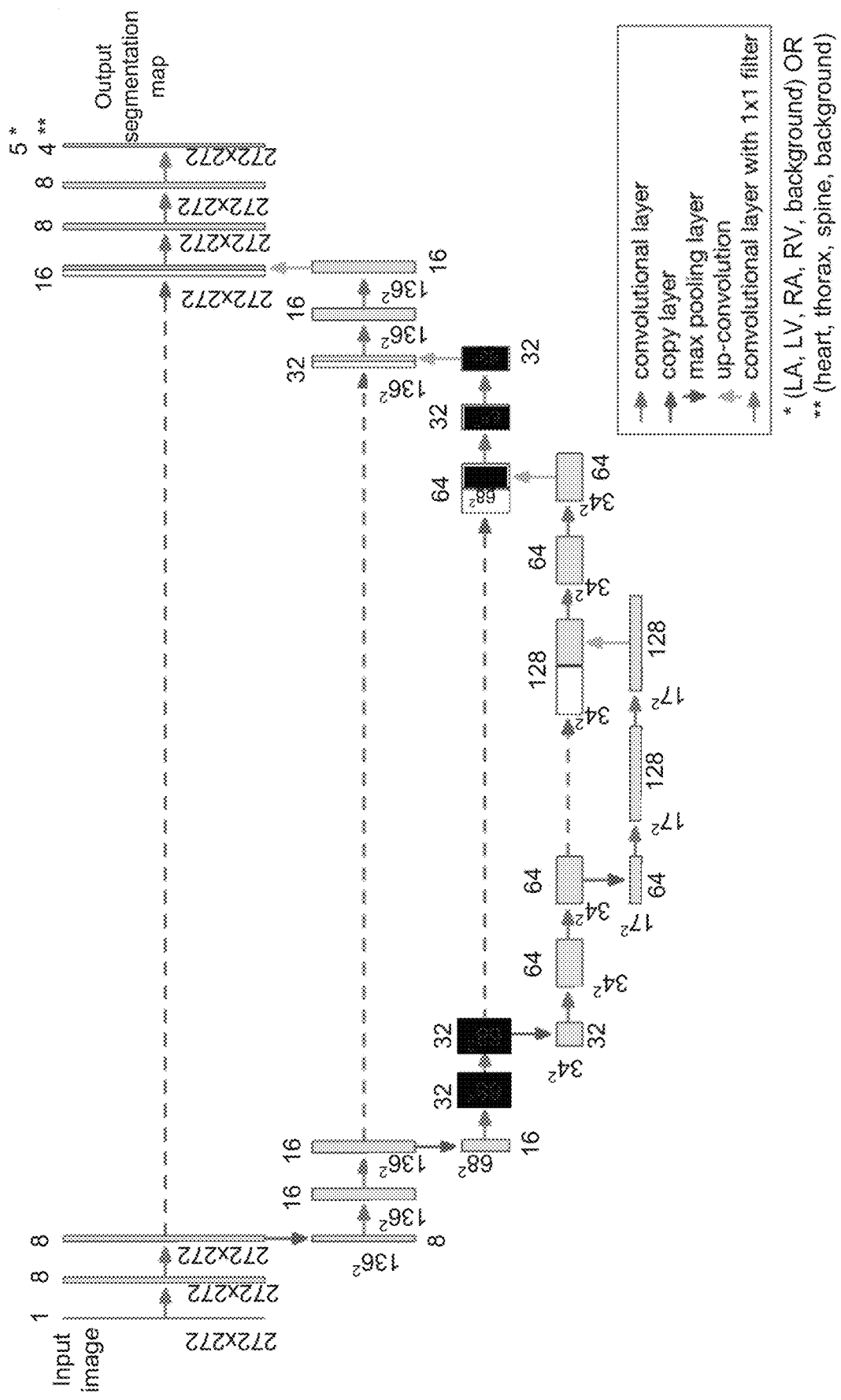
FIG. 10 illustrates an example architecture for segmentation models in accordance with an embodiment of the invention.

An example architecture for segmentation models in accordance with an embodiment of the invention is illustrated in FIG. 10. In this example, the segmentation model is composed of convolutional layers, copy layers, max pooling layers, and up-convolutions. Copy layers in accordance with certain embodiments of the invention can allow a convolutional layer to be used for max pooling, while also feeding the features to a later layer. Segmentation models in accordance with several embodiments of the invention can take an input image and generate an output segmentation map that identifies segments within the image.

Training

Figure 11:
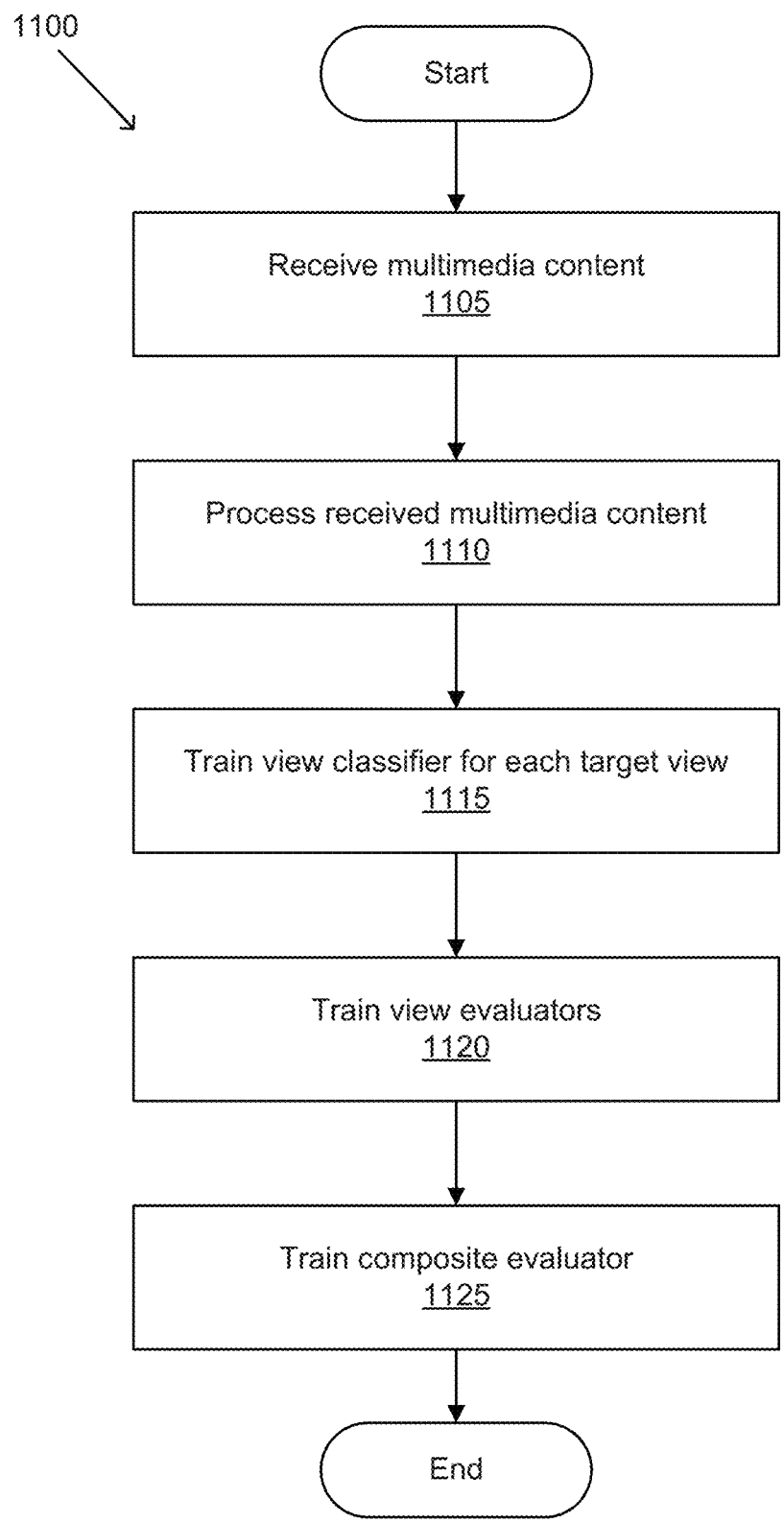
FIG. 11 conceptually illustrates an example of a process for training an evaluation model in accordance with an embodiment of the invention.

An example of a process for training an evaluation model in accordance with an embodiment of the invention is conceptually illustrated in FIG. 11. Process 1100 receives (1105) multimedia content. Multimedia content in accordance with numerous embodiments of the invention can include images and/or video of a subject captured from a variety of different angles. Process 1100 processes (1110) the received multimedia content. Processing the multimedia content, as described above, can include various operations such as (but not limited to) deconstructing video into frames, upscaling, downscaling, normalizing, cropping, and edge detection. In numerous embodiments, training data can be augmented to add variation designed to be clinically relevant. Augmentations can include (but are not limited to) zoom, shear, and/or rotation).

Process 1100 trains (1115) a view classifier for each target view. In many embodiments, processes can train a neural network (e.g., a convolutional neural network (CNN)) to identify frames for each of a number of target screening views from an ultrasound. Target screening views in accordance with several embodiments of the invention can include (but are not limited to) 3-vessel trachea (3VT), 3-vessel view (3VV), apical 5-chamber (A5C), apical 4-chamber (A4C), and/or abdomen (ABDO). Processes in accordance with many embodiments of the invention can use a classifier model that includes classes for each target view, along with an additional class for "non-target" (NT) images. Training data in accordance with various embodiments of the invention can include multiple different and complementary imaging modalities, (for example fetal echocardiograms, enriched for high-quality views of the heart, and fetal surveys, offering a full range of non-target images). In certain embodiments, training data can include data where the view is labeled by experts.

Process 1100 trains (1120) a set of view evaluators. In many embodiments, each view evaluator is trained to classify images from the associated view. For example, each view evaluator can be trained to classify each target image as normal or abnormal. In certain embodiments, view evaluators can be trained to classify images into a number of different classes for different abnormalities.

Biometric measurements can aid in medical screening and diagnosis. In many embodiments, view evaluators can include segmentation engines and/or measurement engines. Segmentation engines in accordance with various embodiments of the invention can be trained to find anatomic structures in target view images. In a number of embodiments, segmentation engines can include (but are not limited to) a convolutional neural network and/or a recurrent neural network. In certain embodiments, segmentation engines can identify various parts of a ultrasound image, such as (but not limited to) the thorax, heart, right atrium (RA), right ventricle (RV), left atrium (LA), left ventricle (LV), spine, and/or background pixels. Measurement engines in accordance with many embodiments of the invention can calculate various measurements, including (but not limited to) cardiothoracic ratio (CTR), cardiac axis (CA), and/or fractional area change (FAC) for each cardiac chamber using segmented structures.

Process 1100 trains (1125) a composite evaluator. Composite evaluators in accordance with several embodiments of the invention can be trained to take, as input, outputs from the view evaluators to predict a diagnosis (e.g., normal vs. abnormal, CHD lesion type, feature vectors, etc.). In a number of embodiments, inputs to a composite evaluator can include (but are not limited to) internal layers (or feature vectors) from a view evaluator, computed measurements, segmented portions, and/or other medical data. Processes in accordance with a number of embodiments of the invention can assemble per-image classifications into a composite diagnostic decision for each heart by applying logistic regression to vectors that summarize predictions on target-view images. Composite evaluators in accordance with a number of embodiments of the invention can be trained to classify the inputs to determine a diagnosis.

In various embodiments, medical imaging tests can be over-read by a trained expert, and any discrepancy between the computer-aided and expert interpretations can be used to train the computerized method. Sensitivity (true positive rate, recall), specificity (true negative rate), and negative predictive value can be reported for the trained model, and updated as the model continues to learn.

In a number of embodiments, confidence levels can be used to train components of an evaluation model. In numerous embodiments, processes can use confidence levels of a view evaluator, segmentation engine, and/or a composite evaluator when training (e.g., as a part of a loss) the other elements of the evaluation model.

Processes in accordance with many embodiments of the invention can determine that image frames from a particular target view are missing (e.g., when no image frames exceed a threshold confidence level for a target view in a view classifier). For example, in the case of heart ultrasound, if a view is missing, it is either missing because it was not acquired well, or, because the heart is so abnormal that that view cannot really be said to exist. Then, the fact that that view is missing, is useful information. In a number of embodiments, the lack of image frames for a particular target view (or "missingness") can be used as an input for other elements of the evaluation model (e.g., view evaluator, a composite evaluator, etc.). For example, processes in accordance with several embodiments of the invention can use a null or zero value as input to the model to indicate that images from a particular target view are missing and/or of low quality (or confidence level).

While specific processes for training are described above, any of a variety of processes can be utilized to train ensemble networks as appropriate to the requirements of specific applications. In certain embodiments, steps may be executed or performed in any order or sequence not limited to the order and sequence shown and described. In a number of embodiments, some of the above steps may be executed or performed substantially simultaneously where appropriate or in parallel to reduce latency and processing times. In some embodiments, one or more of the above steps may be omitted.

Figure 12:
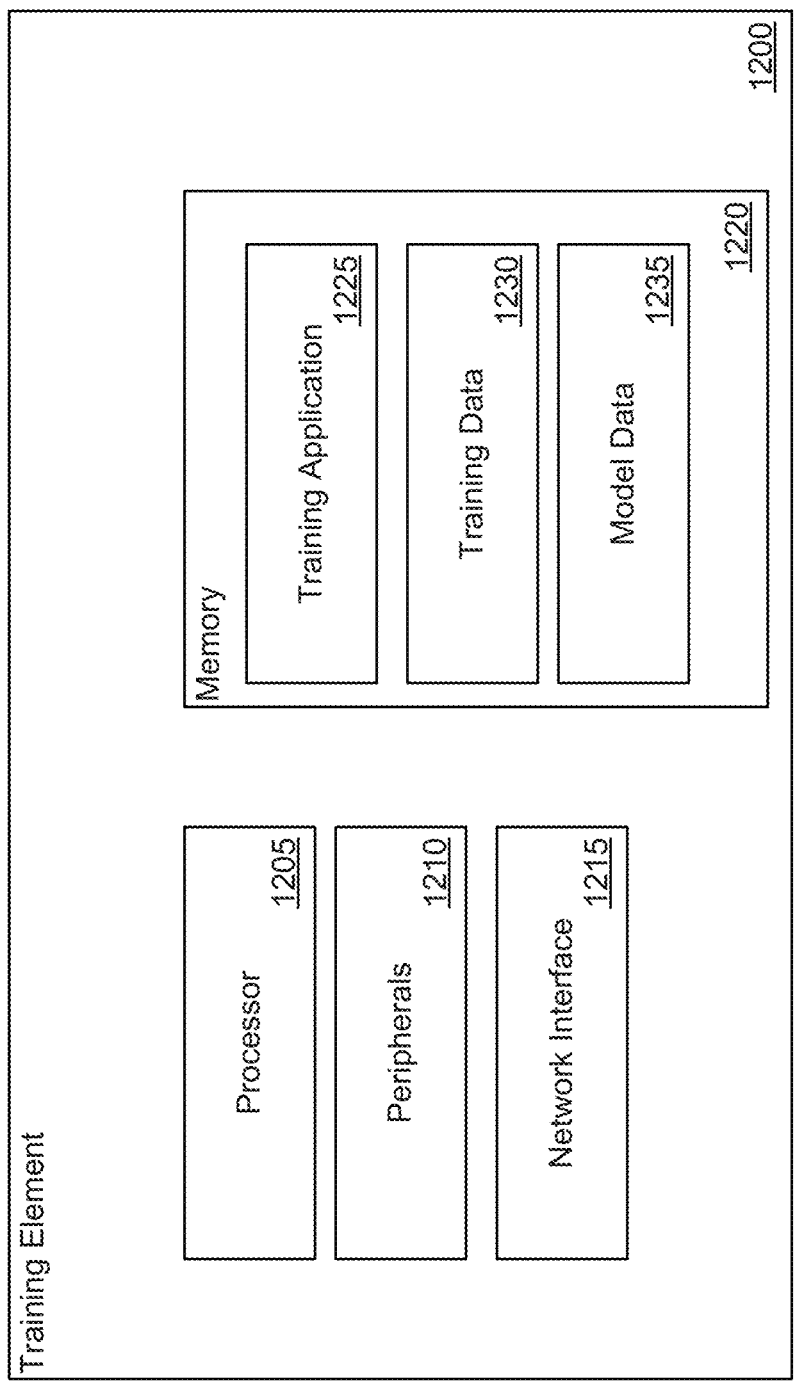
FIG. 12 illustrates an example of a training element in accordance with an embodiment of the invention.

An example of a training element in accordance with an embodiment of the invention is illustrated in FIG. 12. Training elements in accordance with many embodiments of the invention can include (but are not limited to) one or more of mobile devices, cameras, servers, cloud systems, and/or computers. Training element 1200 includes processor 1205, peripherals 1210, network interface 1215, and memory 1220.

One skilled in the art will recognize that a particular training element may include other components that are omitted for brevity without departing from this invention. The processor 1205 can include (but is not limited to) a processor, microprocessor, controller, or a combination of processors, microprocessor, and/or controllers that performs instructions stored in the memory 1220 to manipulate data stored in the memory. Processor instructions can configure the processor 1205 to perform processes in accordance with certain embodiments of the invention.

Peripherals 1210 can include any of a variety of components for capturing data, such as (but not limited to) cameras, displays, and/or sensors. In a variety of embodiments, peripherals can be used to gather inputs and/or provide outputs. Network interface 1215 allows training element 1200 to transmit and receive data over a network based upon the instructions performed by processor 1205. Peripherals and/or network interfaces in accordance with many embodiments of the invention can be used to gather inputs (e.g., labeled images, video, etc.) that can be used to train various parts of an ensemble network. Labels in accordance with certain embodiments of the invention can be identified from existing clinical information and/or manual annotation.

Memory 1220 includes a training application 1225, training data 1230, and model data 1235. Training applications in accordance with several embodiments of the invention can be used to train ensemble networks for evaluating image and/or video data.

Training data in accordance with a variety of embodiments of the invention can include various types of multimedia data that can be used in evaluation processes. In certain embodiments, training data can include (but is not limited to) ultrasound video, images, audio, ground truth labels, etc. Training data in accordance with certain embodiments of the invention can include real data and/or synthetic data for training and testing the models.

In several embodiments, model data can store various parameters and/or weights for ensemble models. Model data in accordance with many embodiments of the invention can be updated through training on training data. In numerous embodiments, model data can include data for several different models, such as (but not limited to) view classifiers, view analyzers, segmenting models, measurement models, and/or composite classifiers.

Although a specific example of a training element 1200 is illustrated in FIG. 12, any of a variety of training elements can be utilized to perform processes for training ensemble systems similar to those described herein as appropriate to the requirements of specific applications in accordance with embodiments of the invention.

Figure 13:
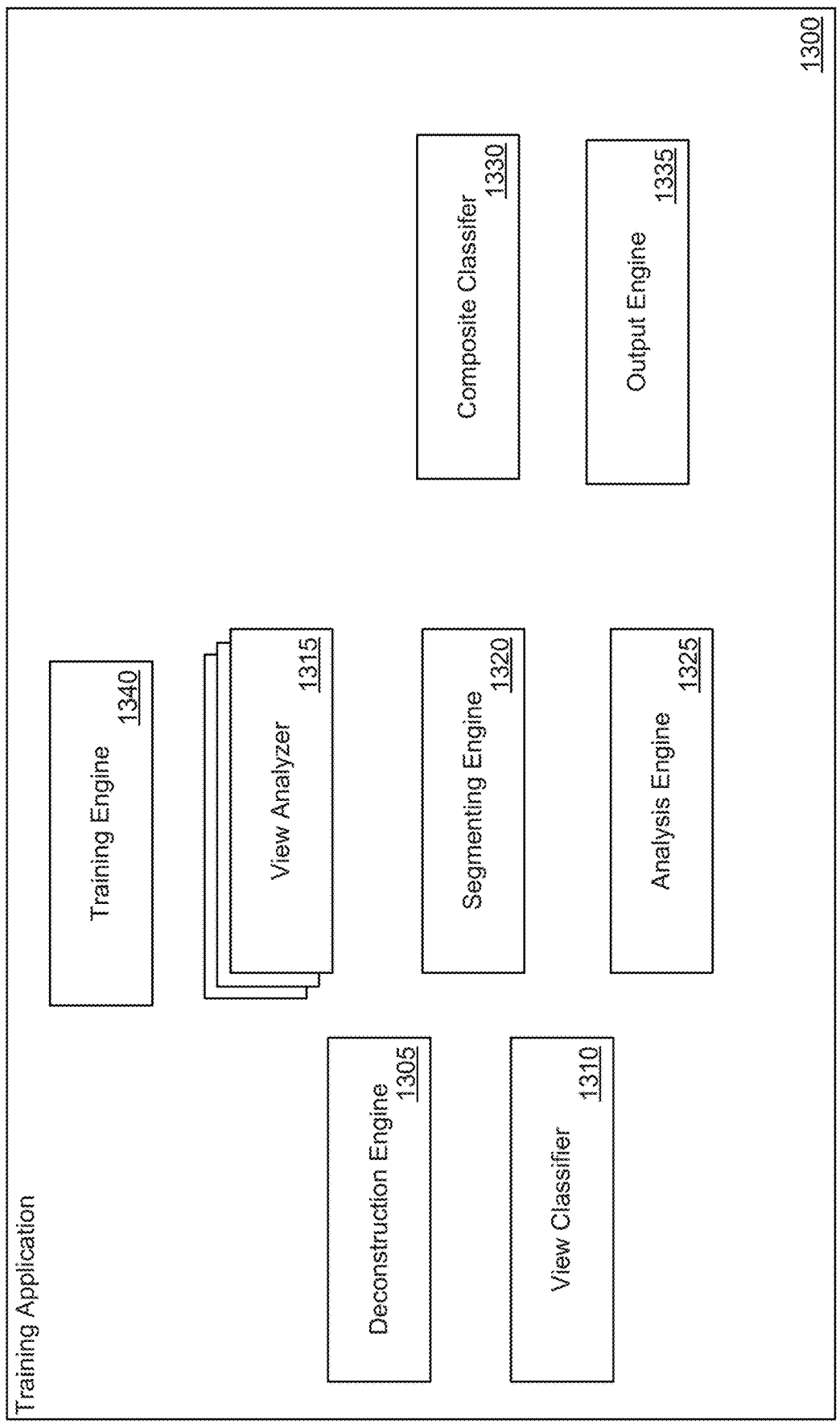
FIG. 13 illustrates an example of a training application in accordance with an embodiment of the invention.

An example of a training application in accordance with an embodiment of the invention is illustrated in FIG. 13. Training applications in accordance with various embodiments of the invention can be used to train ensemble networks for evaluating multimedia content. Similar to evaluation application 800 of FIG. 8, training application 1300 includes deconstruction engine 1305, view classifier 1310, view analyzers 1315, segmenting engine 1320, analysis engine 1325, composite classifier 1330, and output engine 1335. Training application 1300 further includes training engine 1340.

Training engines in accordance with a variety of embodiments of the invention can be used to compute losses and update weights for various models of an ensemble model. In certain embodiments, training engines can compute losses for training samples based on classifications predicted by a model versus a label associated with the training sample. Losses can also be computed based on further feedback received from a user regarding a classification or result of a model. Segmenting engines and analysis engines can be trained based on training images, where ground truth segmenting and/or measurements can be performed manually by a user. In some embodiments, output engines can provide images from each target view and receive feedback regarding whether the images are properly classified, which can be used to train the view analyzers.

Although a specific example of a training application 1300 is illustrated in FIG. 13, any of a variety of training applications can be utilized to perform processes for training similar to those described herein as appropriate to the requirements of specific applications in accordance with embodiments of the invention. For example, applications in accordance with various embodiments of the invention can use more or fewer modules. In a number of embodiments, training may be distributed across multiple applications operating on multiple machines.

System

Figure 14:
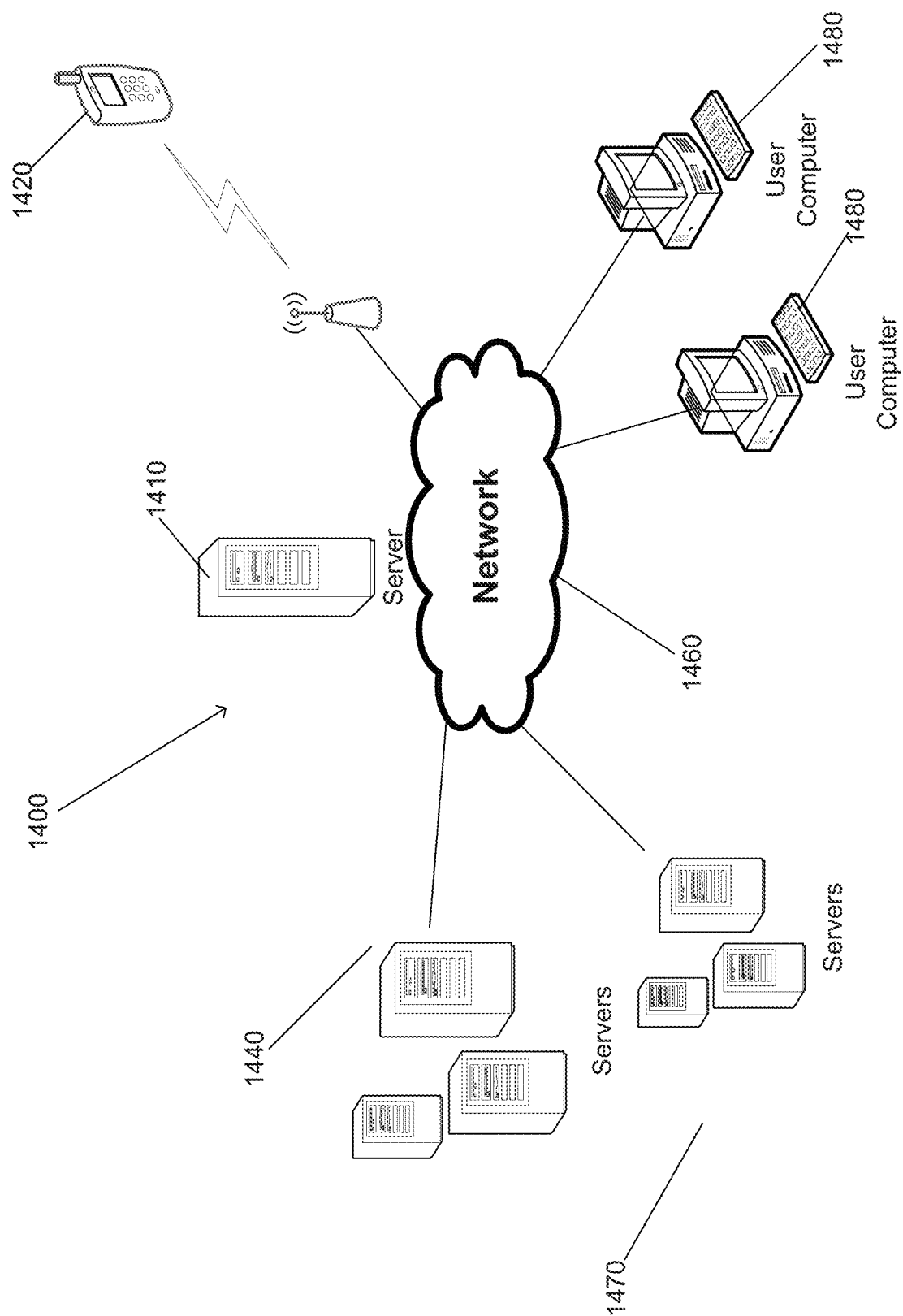
FIG. 14 illustrates an example of an evaluation system in accordance with an embodiment of the invention.

An example of an evaluation system in accordance with an embodiment of the invention is illustrated in FIG. 14. Evaluation systems in accordance with some embodiments of the invention can be used to evaluate multimedia content and/or to train models to perform such evaluations. Evaluation system 1400 includes a communications network 1460. The communications network 1460 is a network such as the Internet that allows devices connected to the network 1460 to communicate with other connected devices. Server systems 1410, 1440, and 1470 are connected to the network 1460. Each of the server systems 1410, 1440, and 1470 is a group of one or more servers communicatively connected to one another via internal networks that execute processes that provide cloud services to users over the network 1460. For purposes of this discussion, cloud services are one or more applications that are executed by one or more server systems to provide data and/or executable applications to devices over a network. The server systems 1410, 1440, and 1470 are shown each having three servers in the internal network. However, the server systems 1410, 1440 and 1470 may include any number of servers and any additional number of server systems may be connected to the network 1460 to provide cloud services. In accordance with various embodiments of this invention, an evaluation system that uses systems and methods that train and evaluate video in accordance with an embodiment of the invention may be provided by a process being executed on a single server system and/or a group of server systems communicating over network 1460.

Users may use devices 1480 and 1420 that connect to the network 1460 to perform processes that train ensemble models, capture image data, and/or evaluate image data in accordance with various embodiments of the invention. In the shown embodiment, the personal devices 1480 are shown as desktop computers that are connected via a conventional "wired" connection to the network 1460. However, the device 1480 may be a desktop computer, a laptop computer, a camera, a smart television, an ultrasound machine, a computed tomography scanner, an X-ray machine, an MRI scanner, a nuclear imaging scanner, an entertainment gaming console, or any other device that connects to the network 1460 via a "wired" connection. The mobile device 1420 connects to network 1460 using a wireless connection. A wireless connection is a connection that uses Radio Frequency (RF) signals, Infrared signals, or any other form of wireless signaling to connect to the network 1460. In FIG. 14, the mobile device 1420 is a mobile telephone. However, mobile device 1420 may be a mobile phone, Personal Digital Assistant (PDA), a tablet, a smartphone, a laptop, a camera, a portable ultrasound machine, a portable radiology scanner, or any other type of device that connects to network 1460 via wireless connection without departing from this invention.

As can readily be appreciated the specific computing system used to train ensemble models and/or evaluate video is largely dependent upon the requirements of a given application and should not be considered as limited to any specific computing system(s) implementation.

Results

Figure 15:
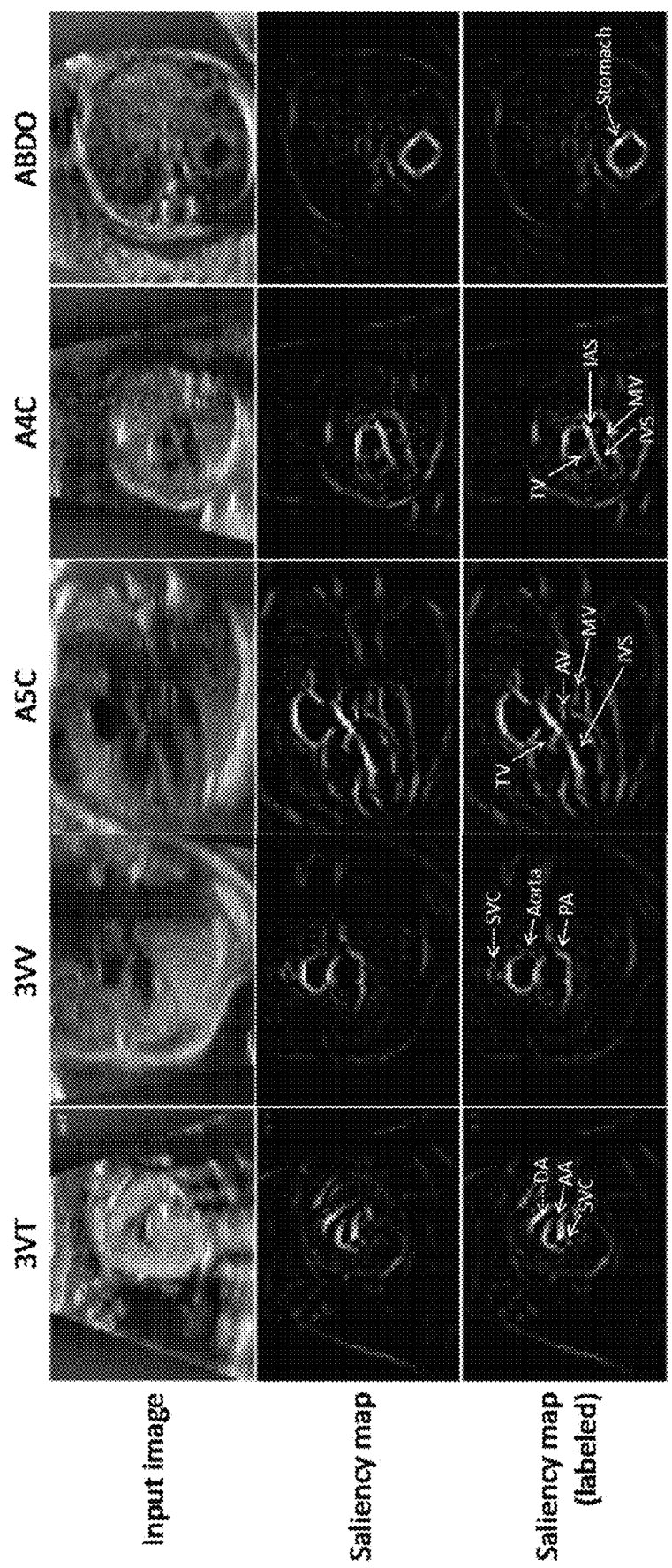
FIG. 15 illustrates saliency maps of view classification in accordance with an embodiment of the invention.

Several analyses were performed to determine whether classification decisions were based on clinically relevant image features—the same anatomic structures that clinicians see. In view classification for fetal heart view classification, the model's area of greatest confusion was between 3VT and 3VV; these adjacent views often cause clinical uncertainty also. Saliency maps can plot the pixels in a given input image that are most important to the model's decision-making. Saliency maps of view classification in accordance with an embodiment of the invention are illustrated in FIG. 15. For each example image given to the trained view classification model, a saliency map shows the pixels most important to the model in predicting the view. This figure shows that anatomic structures relied on by the models are also clinically important to defining a given view.

Figure 16:
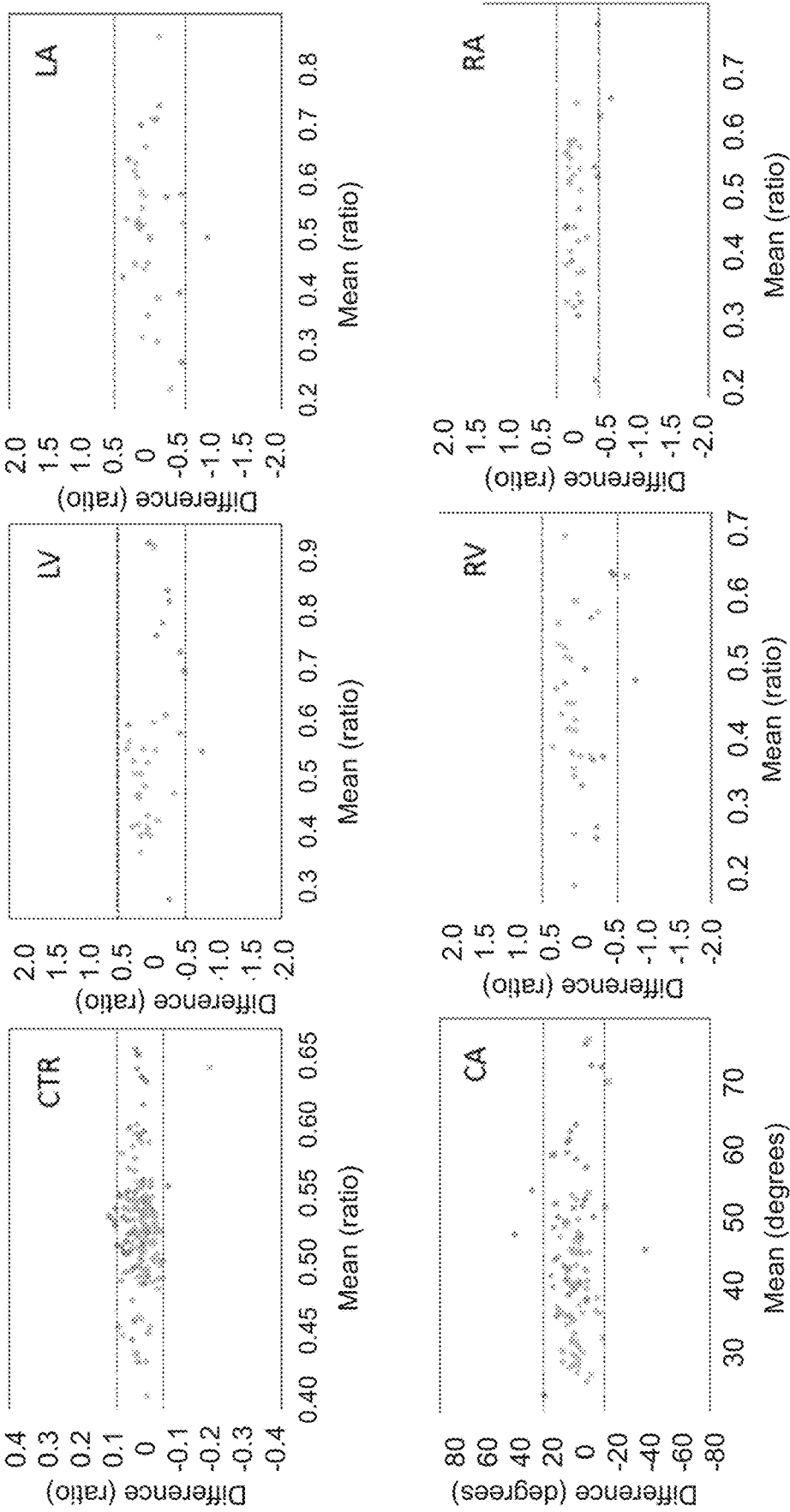
FIG. 16 illustrates plots comparing cardiac measurements from labeled vs. predicted structures.

Bland-Altman plots comparing measurements from labeled vs. predicted cardiac structures are illustrated in FIG. 16. These results show that measurements from predicted structures are generally close to those from labeled structures across various different structures and heart conditions.

Figure 17:
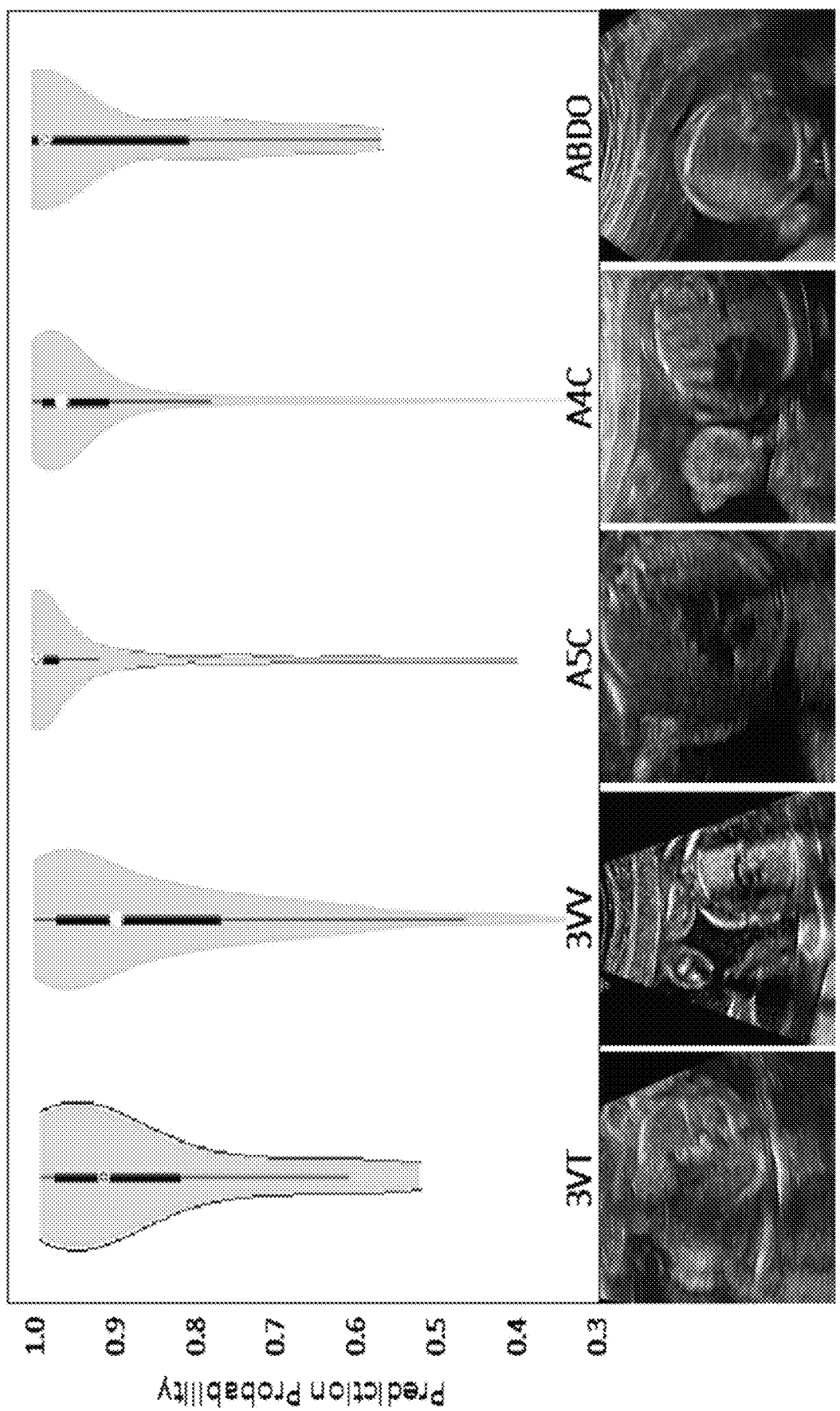
FIG. 17 illustrates examples of model confidence on sub-optimal images.

Models in accordance with many embodiments of the invention can perform well, even on sub-optimal images. Results for model confidence on sub-optimal images are illustrated in FIG. 17. Examples of sub-optimal quality images are shown for each view, along with violin plots showing prediction probabilities assigned to the sub-optimal target images (White dots signify mean, thick black line signifies $1^{st}$ to $3^{rd}$ quartiles).

Importantly, results show that processes in accordance with a variety of embodiments of the invention maintained high performance on datasets from external medical centers and images of sub-optimal quality. testing the model against several different datasets demonstrates that the model performs similar to or better than reported benchmarks for clinical diagnostic tasks.

Although specific methods are discussed above, many different methods can be implemented in accordance with many different embodiments of the invention. It is therefore to be understood that the present invention may be practiced in ways other than specifically described, without departing from the scope and spirit of the present invention. Thus, embodiments of the present invention should be considered in all respects as illustrative and not restrictive. Accordingly, the scope of the invention should be determined not by the embodiments illustrated, but by the appended claims and their equivalents.

What is claimed is:

1. A method for evaluating multimedia content, the method comprising:
receiving multimedia content;
identifying a set of one or more image frames for each of a plurality of target views from the received multimedia content, wherein each image frame in the set of one or more image frames has a probability for classification to a target view in the plurality of target views that exceeds a threshold value;
for each target view, evaluating the corresponding set of image frames to generate an intermediate result, wherein evaluating the corresponding set of image frames for a particular target view comprises determining whether the set of image frames are sufficient for diagnosis; and
determining a composite result based on the intermediate results for each of the plurality of target views, wherein when the images for the particular target view are not sufficient, determining the composite result based on a lack of sufficient image frames.

2. The method of claim 1, wherein the multimedia content comprises video from a medical imaging test.

3. The method of claim 1, wherein identifying the set of image frames comprises deconstructing video from the multimedia content into individual image frames and processing each of the individual image frames.

4. The method of claim 3, wherein processing an image frame comprises performing at least one of edge detection, cropping, and downsampling.

5. The method of claim 1, wherein identifying the set of one or more image frames for each target view comprises classifying image frames from the multimedia content according to one of the plurality of target views.

6. The method of claim 5, wherein classifying the image frames comprises classifying image frames as non-target views.

7. The method of claim 1, wherein evaluating the corresponding set of image frames comprises using a separate evaluation model for each target view of the plurality of target views.

8. The method of claim 7, wherein each separate evaluation model for each target view comprises a classification model trained to reach a same result as the composite result.

9. The method of claim 7, wherein evaluating the corresponding set of image frames comprises using a plurality of evaluation models for at least one target view of the plurality of target views, where the plurality of evaluation models comprises a segmentation model for segmenting image frames of the corresponding set of image frames.

10. The method of claim 9, wherein evaluating the corresponding set of image frames comprises measuring a size of at least one segment in at least two different frames to compute a change in the segment.

11. The method of claim 9, wherein the segmenting image frames comprises segments of empty space within an image frame.

12. The method of claim 7, wherein determining the composite result comprises using a composite model, wherein the composite model takes as input an output of the separate evaluation model for at least one target view of the plurality of target views.

13. The method of claim 7, wherein determining the composite result comprises using a composite model, wherein the composite model takes as input at least one of a segmentation map, a measurement of a region of interest from at least one image, and a classification from the separate evaluation model for at least one target view of the plurality of target views.

14. The method of claim 1, wherein identifying a set of one or more image frames for each of a plurality of target views from the received multimedia content comprises:
evaluating image frames based on the plurality of target views;
determining whether the image frames for each target view are sufficient for diagnosis; and
when the images for a particular target view are not sufficient, providing feedback to a user to capture additional video.

15. The method of claim 14, wherein evaluating image frames comprises determining whether image frames of a quality level greater than a threshold value have been captured for each of the plurality of target views, wherein the quality level is based on a confidence level for a classification.

16. A non-transitory machine readable medium containing processor instructions for evaluating multimedia content, where execution of the instructions by a processor causes the processor to perform a process that comprises:
receiving multimedia content;
identifying a set of one or more image frames for each of a plurality of target views from the received multimedia content, wherein each image frame in the set of one or more image frames has a probability for classification to a target view in the plurality of target views that exceeds a threshold value;
for each target view, evaluating the corresponding set of image frames to generate an intermediate result, wherein evaluating the corresponding set of image frames for a particular target view comprises determining whether the set of image frames are sufficient for diagnosis; and
determining a composite result based on the intermediate results for each of the plurality of target views, wherein when the images for the particular target view are not sufficient, determining a composite result based on a lack of sufficient image frames.

17. The non-transitory machine readable medium of claim 16, wherein the process further comprises deconstructing any videos in a medical imaging test into individual image frames and processing each of the individual image frames.

18. The non-transitory machine readable medium of claim 16, wherein identifying the set of one or more image frames for each target view comprises classifying image frames from a medical imaging test according to one of the plurality of target views.

19. The non-transitory machine readable medium of claim 16, wherein evaluating the corresponding set of image frames comprises using a separate evaluation model for each target view of the plurality of target views.

* * * * *